(12) United States Patent
Wraith

(10) Patent No.: US 8,703,705 B2
(45) Date of Patent: Apr. 22, 2014

(54) MODIFIED FACTOR VIII PEPTIDES

(75) Inventor: David Wraith, Bristol (GB)

(73) Assignee: Apitope International NV, Diepenbeck (BE)

( * ) Notice: Subject to any disclaimer, the term of this patent is extended or adjusted under 35 U.S.C. 154(b) by 0 days.

(21) Appl. No.: 13/320,201

(22) PCT Filed: May 17, 2010

(86) PCT No.: PCT/GB2010/000997
§ 371 (c)(1),
(2), (4) Date: Jan. 30, 2012

(87) PCT Pub. No.: WO2010/133834
PCT Pub. Date: Nov. 25, 2010

(65) Prior Publication Data
US 2012/0121625 A1 May 17, 2012

(30) Foreign Application Priority Data

May 18, 2009 (GB) .................................. 0908515.0

(51) Int. Cl.
*A61K 39/00* (2006.01)
*A61K 38/04* (2006.01)
*C07K 14/755* (2006.01)
*A61K 38/37* (2006.01)

(52) U.S. Cl.
USPC ..................... 514/14.1; 530/327; 424/185.1

(58) Field of Classification Search
None
See application file for complete search history.

(56) References Cited

U.S. PATENT DOCUMENTS

2005/0256304 A1* 11/2005 Jones et al. ................... 530/383

FOREIGN PATENT DOCUMENTS

| WO | WO-0216410 A2 | 2/2002 |
| WO | WO-02060917 A2 | 8/2002 |
| WO | WO-02/096454 A1 | 12/2002 |
| WO | WO-02098454 A2 | 12/2002 |
| WO | WO 02098454 A2 * | 12/2002 |
| WO | WO-03087161 A1 | 10/2003 |
| WO | WO-2009071886 A1 | 6/2009 |
| WO | WO 2009095646 A2 * | 8/2009 |
| WO | WO-2009095646 A2 | 8/2009 |

OTHER PUBLICATIONS

Bowie et al. Deciphering the message in protein sequences:tolerance to amino acid substitutions. Science, 247:1306-1310, 1990.*
Whisstock et al. Prediction of protein function from protein sequence and structure.Quarterly Reviews in Biophysics. 36(3):307- 340, 2007.*

Acharya et al., Management of factor VIII inhibitors.*Best Pract. Res. Clin. Haematol* ., 19(1):51-66 (2006).
Akdis et al., Role of interleukin 10 in specific immunotherapy. *J. Clin. Invest* ., 102(1):98-106 (1998).
Algiman et al., Natural antibodies to factor VIII (anti-hemophilic factor) in healthy individuals. *Proc. Natl. Acad. Sci. U.S.A.*, 89(9):3795-9 (1992).
Anderton et al., Hierarchy in the ability of T cell epitopes to induce peripheral tolerance to antigens from myelin. *Eur. J. Immunol.*, 28(4):1251-61 (1998).
Anderton et al., Mechanisms of central and peripheral T-cell tolerance: lessons from experimental models of multiple sclerosis. *Immunol. Rev.*, 169:123-37 (1999).
Burkhart et al., Peptide-induced T cell regulation of experimental autoimmune encephalomyelitis: a role for IL-10. *Int. Immunol.*, 11(10):1625-34 (1999).
Dimichele, Immune tolerance therapy for factor VIII inhibitors: moving from empiricism to an evidence-based approach. *J. Thromb. Haemost.*, 5 Suppl 1:143-50 (2007).
Fairchild et al., The nature of cryptic epitopes within the self-antigen myelin basic protein. *Int. Immunol.*, 8(7):1035-43 (1996).
Gitschier et al., Characterization of the human factor VIII gene. *Nature*, 312(5992):326-30 (1984).
Hay et al., Current and future approaches to inhibitor management and aversion. *Semin. Thromb. Hemost.*, 32 Suppl 2:15-21 (2006).
International Preliminary Report on Patentability, PCT/ GB2010/000997, International Bureau of WIPO, completed Nov. 22, 2011.
International Search Reporting and Written Opinion of the International Searching Authority, PCT/GB2010/000997, European Patent Office, dated Dec. 29, 2010.
Liu et al., Affinity for class II MHC determines the extent to which soluble peptides tolerize autoreactive T cells in naive and primed adult mice—implications for autoimmunity. *Int. Immunol.*, 7(8):1255-63 (1995).
Metzler et al., Inhibition of experimental autoimmune encephalomyelitis by inhalation but not oral administration of the encephalitogenic peptide: influence of MHC binding affinity. *Int. Immunol.*, 5(9):1159-65 (1993).
Moreau et al., Antibodies to the FVIII light chain that neutralize FVIII procoagulant activity are present in plasma of nonresponder patients with severe hemophilia A and in normal polyclonal human IgG. *Blood*, 95(11):3435-41 (2000).
Müller et al., Successful immunotherapy with T-cell epitope peptides of bee venom phospholipase A2 induces specific T-cell anergy in patients allergic to bee venom. *J. Allergy Clin. Immunol.*, 101(6 Pt 1):747-54 (1998).

(Continued)

*Primary Examiner* — Vanessa L Ford
*Assistant Examiner* — Sandra Dillahunt
(74) *Attorney, Agent, or Firm* — Marshall, Gerstein & Borun LLP

(57) ABSTRACT

The present invention provides peptides at least partly derivable from FVIII which are capable of binding to an MHC class II molecule without further antigen processing and being recognized by a factor VIII specific T cell. In particular, the present invention provides a peptide comprising or consisting of the sequence EDNIMVTFRNQASR. The present invention also relates to the use of such a peptide for the prevention or suppression of inhibitor antibody formation in haemophilia A and/or acquired haemophilia.

10 Claims, 15 Drawing Sheets

(56) References Cited

OTHER PUBLICATIONS

Nelson et al., T-T hybridoma product specifically suppresses tumor immunity. *Proc. Natl. Acad. Sci. U.S.A.*, 77(5):2866-70 (1980).
Reding, Immunological aspects of inhibitor development. *Haemophilia*, 12 Suppl 6:30-5 (2006).
Roberge et al., A strategy for a convergent synthesis of N-linked glycopeptides on a solid support. *Science*, 269(5221):202-4 (1995).
Summers et al., Phenotypic characterization of five dendritic cell subsets in human tonsils. *Am. J. Pathol.*, 159(1):285-95 (2001).
Wood et al., Expression of active human factor VII from recombinant DNA clones. Nature, 312(5992):330-7 (1984).
Ananyeva, et al., "Inhibitors in Hemophilia A: Mechanisms of Inhibitation, Management and Perspectives," Blood Coagulation & Fibrinolysis, vol. 15, No. 2, p. 109-124 (2004).

* cited by examiner

SEQUENCE LISTING

<160> NUMBER OF SEQ ID NOS: 83

<210> SEQ ID NO 1
<211> LENGTH: 2351
<212> TYPE: PRT
<213> ORGANISM: Homo sapiens

<400> SEQUENCE: 1

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

```
Ala Lys Pro Arg Pro Trp Met Gly Leu Gly Pro Thr Ile Gln
             85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
            115                 120                 125

Glu Gly Ala Glu Tyr Asp Asp Gln Thr Ser Gln Arg Glu Lys Glu Asp
            130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
            195                 200                 205

Gln Thr Leu His Lys Phe Ile Leu Leu Phe Ala Val Phe Asp Glu Gly
            210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
            290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
            370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
            450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510
```

-continued

```
Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
        770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
            820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
930                 935                 940
```

-continued

```
Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
                980                 985                 990

Lys Gly Lys Arg Ala His Gly Pro Ala Leu Leu Thr Lys Asp Asn Ala
            995                1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Lys Lys Val Thr Pro Leu Ile His Asp Arg
    1055                1060                1065

Met Leu Met Asp Lys Asn Ala Thr Ala Leu Arg Leu Asn His Met
    1070                1075                1080

Ser Asn Lys Thr Thr Ser Ser Lys Asn Met Glu Met Val Gln Gln
    1085                1090                1095

Lys Lys Glu Gly Pro Ile Pro Pro Asp Ala Gln Asn Pro Asp Met
    1100                1105                1110

Ser Phe Phe Lys Met Leu Phe Leu Pro Glu Ser Ala Arg Trp Ile
    1115                1120                1125

Gln Arg Thr His Gly Lys Asn Ser Leu Asn Ser Gly Gln Gly Pro
    1130                1135                1140

Ser Pro Lys Gln Leu Val Ser Leu Gly Pro Glu Lys Ser Val Glu
    1145                1150                1155

Gly Gln Asn Phe Leu Ser Glu Lys Asn Lys Val Val Val Gly Lys
    1160                1165                1170

Gly Glu Phe Thr Lys Asp Val Gly Leu Lys Glu Met Val Phe Pro
    1175                1180                1185

Ser Ser Arg Asn Leu Phe Leu Thr Asn Leu Asp Asn Leu His Glu
    1190                1195                1200

Asn Asn Thr His Asn Gln Glu Lys Lys Ile Gln Glu Glu Ile Glu
    1205                1210                1215

Lys Lys Glu Thr Leu Ile Gln Glu Asn Val Val Leu Pro Gln Ile
    1220                1225                1230

His Thr Val Thr Gly Thr Lys Asn Phe Met Lys Asn Leu Phe Leu
    1235                1240                1245

Leu Ser Thr Arg Gln Asn Val Glu Gly Ser Tyr Asp Gly Ala Tyr
    1250                1255                1260

Ala Pro Val Leu Gln Asp Phe Arg Ser Leu Asn Asp Ser Thr Asn
    1265                1270                1275

Arg Thr Lys Lys His Thr Ala His Phe Ser Lys Lys Gly Glu Glu
    1280                1285                1290

Glu Asn Leu Glu Gly Leu Gly Asn Gln Thr Lys Gln Ile Val Glu
    1295                1300                1305

Lys Tyr Ala Cys Thr Thr Arg Ile Ser Pro Asn Thr Ser Gln Gln
    1310                1315                1320

Asn Phe Val Thr Gln Arg Ser Lys Arg Ala Leu Lys Gln Phe Arg
    1325                1330                1335

Leu Pro Leu Glu Glu Thr Glu Leu Glu Lys Arg Ile Ile Val Asp
    1340                1345                1350
```

-continued

Asp Thr Ser Thr Gln Trp Ser Lys Asn Met Lys His Leu Thr Pro
1355                1360                1365

Ser Thr Leu Thr Gln Ile Asp Tyr Asn Glu Lys Glu Lys Gly Ala
1370                1375                1380

Ile Thr Gln Ser Pro Leu Ser Asp Cys Leu Thr Arg Ser His Ser
1385                1390                1395

Ile Pro Gln Ala Asn Arg Ser Pro Leu Pro Ile Ala Lys Val Ser
1400                1405                1410

Ser Phe Pro Ser Ile Arg Pro Ile Tyr Leu Thr Arg Val Leu Phe
1415                1420                1425

Gln Asp Asn Ser Ser His Leu Pro Ala Ala Ser Tyr Arg Lys Lys
1430                1435                1440

Asp Ser Gly Val Gln Glu Ser Ser His Phe Leu Gln Gly Ala Lys
1445                1450                1455

Lys Asn Asn Leu Ser Leu Ala Ile Leu Thr Leu Glu Met Thr Gly
1460                1465                1470

Asp Gln Arg Glu Val Gly Ser Leu Gly Thr Ser Ala Thr Asn Ser
1475                1480                1485

Val Thr Tyr Lys Lys Val Glu Asn Thr Val Leu Pro Lys Pro Asp
1490                1495                1500

Leu Pro Lys Thr Ser Gly Lys Val Glu Leu Leu Pro Lys Val His
1505                1510                1515

Ile Tyr Gln Lys Asp Leu Phe Pro Thr Glu Thr Ser Asn Gly Ser
1520                1525                1530

Pro Gly His Leu Asp Leu Val Glu Gly Ser Leu Leu Gln Gly Thr
1535                1540                1545

Glu Gly Ala Ile Lys Trp Asn Glu Ala Asn Arg Pro Gly Lys Val
1550                1555                1560

Pro Phe Leu Arg Val Ala Thr Glu Ser Ser Ala Lys Thr Pro Ser
1565                1570                1575

Lys Leu Leu Asp Pro Leu Ala Trp Asp Asn His Tyr Gly Thr Gln
1580                1585                1590

Ile Pro Lys Glu Glu Trp Lys Ser Gln Glu Lys Ser Pro Glu Lys
1595                1600                1605

Thr Ala Phe Lys Lys Lys Asp Thr Ile Leu Ser Leu Asn Ala Cys
1610                1615                1620

Glu Ser Asn His Ala Ile Ala Ala Ile Asn Glu Gly Gln Asn Lys
1625                1630                1635

Pro Glu Ile Glu Val Thr Trp Ala Lys Gln Gly Arg Thr Glu Arg
1640                1645                1650

Leu Cys Ser Gln Asn Pro Pro Val Leu Lys Arg His Gln Arg Glu
1655                1660                1665

Ile Thr Arg Thr Thr Leu Gln Ser Asp Gln Glu Glu Ile Asp Tyr
1670                1675                1680

Asp Asp Thr Ile Ser Val Glu Met Lys Lys Glu Asp Phe Asp Ile
1685                1690                1695

Tyr Asp Glu Asp Glu Asn Gln Ser Pro Arg Ser Phe Gln Lys Lys
1700                1705                1710

Thr Arg His Tyr Phe Ile Ala Ala Val Glu Arg Leu Trp Asp Tyr
1715                1720                1725

Gly Met Ser Ser Ser Pro His Val Leu Arg Asn Arg Ala Gln Ser
1730                1735                1740

Gly Ser Val Pro Gln Phe Lys Lys Val Val Phe Gln Glu Phe Thr
1745                1750                1755

-continued

```
Asp Gly Ser Phe Thr Gln Pro Leu Tyr Arg Gly Glu Leu Asn Glu
1760                1765                1770

His Leu Gly Leu Leu Gly Pro Tyr Ile Arg Ala Glu Val Glu Asp
1775                1780                1785

Asn Ile Met Val Thr Phe Arg Asn Gln Ala Ser Arg Pro Tyr Ser
1790                1795                1800

Phe Tyr Ser Ser Leu Ile Ser Tyr Glu Glu Asp Gln Arg Gln Gly
1805                1810                1815

Ala Glu Pro Arg Lys Asn Phe Val Lys Pro Asn Glu Thr Lys Thr
1820                1825                1830

Tyr Phe Trp Lys Val Gln His His Met Ala Pro Thr Lys Asp Glu
1835                1840                1845

Phe Asp Cys Lys Ala Trp Ala Tyr Phe Ser Asp Val Asp Leu Glu
1850                1855                1860

Lys Asp Val His Ser Gly Leu Ile Gly Pro Leu Leu Val Cys His
1865                1870                1875

Thr Asn Thr Leu Asn Pro Ala His Gly Arg Gln Val Thr Val Gln
1880                1885                1890

Glu Phe Ala Leu Phe Phe Thr Ile Phe Asp Glu Thr Lys Ser Trp
1895                1900                1905

Tyr Phe Thr Glu Asn Met Glu Arg Asn Cys Arg Ala Pro Cys Asn
1910                1915                1920

Ile Gln Met Glu Asp Pro Thr Phe Lys Glu Asn Tyr Arg Phe His
1925                1930                1935

Ala Ile Asn Gly Tyr Ile Met Asp Thr Leu Pro Gly Leu Val Met
1940                1945                1950

Ala Gln Asp Gln Arg Ile Arg Trp Tyr Leu Leu Ser Met Gly Ser
1955                1960                1965

Asn Glu Asn Ile His Ser Ile His Phe Ser Gly His Val Phe Thr
1970                1975                1980

Val Arg Lys Lys Glu Glu Tyr Lys Met Ala Leu Tyr Asn Leu Tyr
1985                1990                1995

Pro Gly Val Phe Glu Thr Val Glu Met Leu Pro Ser Lys Ala Gly
2000                2005                2010

Ile Trp Arg Val Glu Cys Leu Ile Gly Glu His Leu His Ala Gly
2015                2020                2025

Met Ser Thr Leu Phe Leu Val Tyr Ser Asn Lys Cys Gln Thr Pro
2030                2035                2040

Leu Gly Met Ala Ser Gly His Ile Arg Asp Phe Gln Ile Thr Ala
2045                2050                2055

Ser Gly Gln Tyr Gly Gln Trp Ala Pro Lys Leu Ala Arg Leu His
2060                2065                2070

Tyr Ser Gly Ser Ile Asn Ala Trp Ser Thr Lys Glu Pro Phe Ser
2075                2080                2085

Trp Ile Lys Val Asp Leu Leu Ala Pro Met Ile Ile His Gly Ile
2090                2095                2100

Lys Thr Gln Gly Ala Arg Gln Lys Phe Ser Ser Leu Tyr Ile Ser
2105                2110                2115

Gln Phe Ile Ile Met Tyr Ser Leu Asp Gly Lys Lys Trp Gln Thr
2120                2125                2130

Tyr Arg Gly Asn Ser Thr Gly Thr Leu Met Val Phe Phe Gly Asn
2135                2140                2145

Val Asp Ser Ser Gly Ile Lys His Asn Ile Phe Asn Pro Pro Ile
2150                2155                2160
```

-continued

```
Ile Ala Arg Tyr Ile Arg Leu His Pro Thr His Tyr Ser Ile Arg
    2165                2170                2175

Ser Thr Leu Arg Met Glu Trp Met Gly Cys Asp Leu Asn Ser Cys
    2180                2185                2190

Ser Met Pro Leu Gly Met Glu Ser Lys Ala Ile Ser Asp Ala Gln
    2195                2200                2205

Ile Thr Ala Ser Ser Tyr Phe Thr Asn Met Phe Ala Thr Trp Ser
    2210                2215                2220

Pro Ser Lys Ala Arg Leu His Leu Gln Gly Arg Ser Asn Ala Trp
    2225                2230                2235

Arg Pro Gln Val Asn Asn Pro Lys Glu Trp Leu Gln Val Asp Phe
    2240                2245                2250

Gln Lys Thr Met Lys Val Thr Gly Val Thr Thr Gln Gly Val Lys
    2255                2260                2265

Ser Leu Leu Thr Ser Met Tyr Val Lys Glu Phe Leu Ile Ser Ser
    2270                2275                2280

Ser Gln Asp Gly His Gln Trp Thr Leu Phe Phe Gln Asn Gly Lys
    2285                2290                2295

Val Lys Val Phe Gln Gly Asn Gln Asp Ser Phe Thr Pro Val Val
    2300                2305                2310

Asn Ser Leu Asp Pro Pro Leu Leu Thr Arg Tyr Leu Arg Ile His
    2315                2320                2325

Pro Gln Ser Trp Val His Gln Ile Ala Leu Arg Met Glu Val Leu
    2330                2335                2340

Gly Cys Glu Ala Gln Asp Leu Tyr
    2345                2350

<210> SEQ ID NO 2
<211> LENGTH: 15
<212> TYPE: PRT
<213> ORGANISM: Homo sapiens

<400> SEQUENCE: 2

Thr Gln Thr Leu His Lys Phe Ile Leu Leu Phe Ala Val Phe Asp
1               5                   10                  15

<210> SEQ ID NO 3
<211> LENGTH: 15
<212> TYPE: PRT
<213> ORGANISM: Homo sapiens

<400> SEQUENCE: 3

Ser Leu Tyr Ile Ser Gln Phe Ile Ile Met Tyr Ser Leu Asp Gly
1               5                   10                  15

<210> SEQ ID NO 4
<211> LENGTH: 15
<212> TYPE: PRT
<213> ORGANISM: Homo sapiens

<400> SEQUENCE: 4

Pro Pro Ile Ile Ala Arg Tyr Ile Arg Leu His Pro Thr His Tyr
1               5                   10                  15

<210> SEQ ID NO 5
<211> LENGTH: 15
<212> TYPE: PRT
```

-continued

```
<400> SEQUENCE: 5

Pro Pro Leu Leu Thr Arg Tyr Leu Arg Ile His Pro Gln Ser Trp
1               5                   10                  15

<210> SEQ ID NO 6
<211> LENGTH: 15
<212> TYPE: PRT
<213> ORGANISM: Homo sapiens

<400> SEQUENCE: 6

Met His Thr Val Asn Gly Tyr Val Asn Arg Ser Leu Pro Gly Leu
1               5                   10                  15

<210> SEQ ID NO 7
<211> LENGTH: 15
<212> TYPE: PRT
<213> ORGANISM: Homo sapiens

<400> SEQUENCE: 7

Leu Gly Gln Phe Leu Leu Phe Cys His Ile Ser Ser His Gln His
1               5                   10                  15

<210> SEQ ID NO 8
<211> LENGTH: 15
<212> TYPE: PRT
<213> ORGANISM: Homo sapiens

<400> SEQUENCE: 8

Asp Thr Leu Leu Ile Ile Phe Lys Asn Gln Ala Ser Arg Pro Tyr
1               5                   10                  15

<210> SEQ ID NO 9
<211> LENGTH: 15
<212> TYPE: PRT
<213> ORGANISM: Homo sapiens

<400> SEQUENCE: 9

Pro Arg Cys Leu Thr Arg Tyr Tyr Ser Ser Phe Val Asn Met Glu
1               5                   10                  15

<210> SEQ ID NO 10
<211> LENGTH: 15
<212> TYPE: PRT
<213> ORGANISM: Homo sapiens

<400> SEQUENCE: 10

Thr Glu Asn Ile Gln Arg Phe Leu Pro Asn Pro Ala Gly Val Gln
1               5                   10                  15

<210> SEQ ID NO 11
<211> LENGTH: 15
<212> TYPE: PRT
<213> ORGANISM: Homo sapiens

<400> SEQUENCE: 11

Asp Asn Ile Met Val Thr Phe Arg Asn Gln Ala Ser Arg Pro Tyr
1               5                   10                  15

<210> SEQ ID NO 12
<211> LENGTH: 15
<212> TYPE: PRT
<213> ORGANISM: Homo sapiens
```

```
<400> SEQUENCE: 12

Arg Tyr Leu Arg Ile His Pro Gln Ser Trp Val His Gln Ile Ala
1               5                   10                  15

<210> SEQ ID NO 13
<211> LENGTH: 15
<212> TYPE: PRT
<213> ORGANISM: Homo sapiens

<400> SEQUENCE: 13

Gly Thr Leu Met Val Phe Phe Gly Asn Val Asp Ser Ser Gly Ile
1               5                   10                  15

<210> SEQ ID NO 14
<211> LENGTH: 9
<212> TYPE: PRT
<213> ORGANISM: Homo sapiens

<400> SEQUENCE: 14

Leu Tyr Ile Ser Gln Phe Ile Ile Met
1               5

<210> SEQ ID NO 15
<211> LENGTH: 9
<212> TYPE: PRT
<213> ORGANISM: Homo sapiens

<400> SEQUENCE: 15

Phe Ile Ile Met Tyr Ser Leu Asp Gly
1               5

<210> SEQ ID NO 16
<211> LENGTH: 9
<212> TYPE: PRT
<213> ORGANISM: Homo sapiens

<400> SEQUENCE: 16

Ile Ala Arg Tyr Ile Arg Leu His Pro
1               5

<210> SEQ ID NO 17
<211> LENGTH: 9
<212> TYPE: PRT
<213> ORGANISM: Homo sapiens

<400> SEQUENCE: 17

Leu Ile Ile Phe Lys Asn Gln Ala Ser
1               5

<210> SEQ ID NO 18
<211> LENGTH: 9
<212> TYPE: PRT
<213> ORGANISM: Homo sapiens

<400> SEQUENCE: 18

Leu Thr Arg Tyr Tyr Ser Ser Phe Val
1               5

<210> SEQ ID NO 19
<211> LENGTH: 9
<212> TYPE: PRT
<213> ORGANISM: Homo sapiens
```

```
<400> SEQUENCE: 19

Met Val Thr Phe Arg Asn Gln Ala Ser
1               5

<210> SEQ ID NO 20
<211> LENGTH: 9
<212> TYPE: PRT
<213> ORGANISM: Homo sapiens

<400> SEQUENCE: 20

Leu Arg Ile His Pro Gln Ser Trp Val
1               5

<210> SEQ ID NO 21
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is a charged hydrophilic amino acid residue

<400> SEQUENCE: 21

Xaa Asp Asn Ile Met Val Thr Phe Arg Asn Gln Ala Ser
1               5                   10

<210> SEQ ID NO 22
<211> LENGTH: 14
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is a charged amino acid with reverse
      polarity to Xaa at position 14
<220> FEATURE:
<221> NAME/KEY: MISC_FEATURE
<222> LOCATION: (14)..(14)
<223> OTHER INFORMATION: Xaa is a charged amino acid with reverse
      polarity to Xaa at position 1

<400> SEQUENCE: 22

Xaa Asp Asn Ile Met Val Thr Phe Arg Asn Gln Ala Ser Xaa
1               5                   10

<210> SEQ ID NO 23
<211> LENGTH: 14
<212> TYPE: PRT
<213> ORGANISM: Homo sapiens

<400> SEQUENCE: 23

Glu Asp Asn Ile Met Val Thr Phe Arg Asn Gln Ala Ser Arg
1               5                   10

<210> SEQ ID NO 24
<211> LENGTH: 15
<212> TYPE: PRT
<213> ORGANISM: Homo sapiens

<400> SEQUENCE: 24

Tyr Gly Glu Val Gly Asp Thr Leu Leu Ile Ile Phe Lys Asn Gln
1               5                   10                  15

<210> SEQ ID NO 25
<211> LENGTH: 15
<212> TYPE: PRT
<213> ORGANISM: Homo sapiens
```

```
<400> SEQUENCE: 25

Gly Glu Val Gly Asp Thr Leu Leu Ile Ile Phe Lys Asn Gln Ala
1               5                   10                  15

<210> SEQ ID NO 26
<211> LENGTH: 15
<212> TYPE: PRT
<213> ORGANISM: Homo sapiens

<400> SEQUENCE: 26

Glu Val Gly Asp Thr Leu Leu Ile Ile Phe Lys Asn Gln Ala Ser
1               5                   10                  15

<210> SEQ ID NO 27
<211> LENGTH: 15
<212> TYPE: PRT
<213> ORGANISM: Homo sapiens

<400> SEQUENCE: 27

Val Gly Asp Thr Leu Leu Ile Ile Phe Lys Asn Gln Ala Ser Arg
1               5                   10                  15

<210> SEQ ID NO 28
<211> LENGTH: 15
<212> TYPE: PRT
<213> ORGANISM: Homo sapiens

<400> SEQUENCE: 28

Gly Asp Thr Leu Leu Ile Ile Phe Lys Asn Gln Ala Ser Arg Pro
1               5                   10                  15

<210> SEQ ID NO 29
<211> LENGTH: 15
<212> TYPE: PRT
<213> ORGANISM: Homo sapiens

<400> SEQUENCE: 29

Thr Leu Leu Ile Ile Phe Lys Asn Gln Ala Ser Arg Pro Tyr Asn
1               5                   10                  15

<210> SEQ ID NO 30
<211> LENGTH: 15
<212> TYPE: PRT
<213> ORGANISM: Homo sapiens

<400> SEQUENCE: 30

Leu Leu Ile Ile Phe Lys Asn Gln Ala Ser Arg Pro Tyr Asn Ile
1               5                   10                  15

<210> SEQ ID NO 31
<211> LENGTH: 15
<212> TYPE: PRT
<213> ORGANISM: Homo sapiens

<400> SEQUENCE: 31

Leu Ile Ile Phe Lys Asn Gln Ala Ser Arg Pro Tyr Asn Ile Tyr
1               5                   10                  15

<210> SEQ ID NO 32
<211> LENGTH: 15
<212> TYPE: PRT
<213> ORGANISM: Homo sapiens
```

```
<400> SEQUENCE: 32

Ile Ile Phe Lys Asn Gln Ala Ser Arg Pro Tyr Asn Ile Tyr Pro
1               5                   10                  15

<210> SEQ ID NO 33
<211> LENGTH: 15
<212> TYPE: PRT
<213> ORGANISM: Homo sapiens

<400> SEQUENCE: 33

Ile Phe Lys Asn Gln Ala Ser Arg Pro Tyr Asn Ile Tyr Pro His
1               5                   10                  15

<210> SEQ ID NO 34
<211> LENGTH: 15
<212> TYPE: PRT
<213> ORGANISM: Homo sapiens

<400> SEQUENCE: 34

Pro Thr Lys Ser Asp Pro Arg Cys Leu Thr Arg Tyr Tyr Ser Ser
1               5                   10                  15

<210> SEQ ID NO 35
<211> LENGTH: 15
<212> TYPE: PRT
<213> ORGANISM: Homo sapiens

<400> SEQUENCE: 35

Thr Lys Ser Asp Pro Arg Cys Leu Thr Arg Tyr Tyr Ser Ser Phe
1               5                   10                  15

<210> SEQ ID NO 36
<211> LENGTH: 15
<212> TYPE: PRT
<213> ORGANISM: Homo sapiens

<400> SEQUENCE: 36

Lys Ser Asp Pro Arg Cys Leu Thr Arg Tyr Tyr Ser Ser Phe Val
1               5                   10                  15

<210> SEQ ID NO 37
<211> LENGTH: 15
<212> TYPE: PRT
<213> ORGANISM: Homo sapiens

<400> SEQUENCE: 37

Ser Asp Pro Arg Cys Leu Thr Arg Tyr Tyr Ser Ser Phe Val Asn
1               5                   10                  15

<210> SEQ ID NO 38
<211> LENGTH: 15
<212> TYPE: PRT
<213> ORGANISM: Homo sapiens

<400> SEQUENCE: 38

Asp Pro Arg Cys Leu Thr Arg Tyr Tyr Ser Ser Phe Val Asn Met
1               5                   10                  15

<210> SEQ ID NO 39
<211> LENGTH: 15
<212> TYPE: PRT
<213> ORGANISM: Homo sapiens
```

-continued

```
<400> SEQUENCE: 39

Arg Cys Leu Thr Arg Tyr Tyr Ser Ser Phe Val Asn Met Glu Arg
1               5                   10                  15

<210> SEQ ID NO 40
<211> LENGTH: 15
<212> TYPE: PRT
<213> ORGANISM: Homo sapiens

<400> SEQUENCE: 40

Cys Leu Thr Arg Tyr Tyr Ser Ser Phe Val Asn Met Glu Arg Asp
1               5                   10                  15

<210> SEQ ID NO 41
<211> LENGTH: 15
<212> TYPE: PRT
<213> ORGANISM: Homo sapiens

<400> SEQUENCE: 41

Leu Thr Arg Tyr Tyr Ser Ser Phe Val Asn Met Glu Arg Asp Leu
1               5                   10                  15

<210> SEQ ID NO 42
<211> LENGTH: 15
<212> TYPE: PRT
<213> ORGANISM: Homo sapiens

<400> SEQUENCE: 42

Thr Arg Tyr Tyr Ser Ser Phe Val Asn Met Glu Arg Asp Leu Ala
1               5                   10                  15

<210> SEQ ID NO 43
<211> LENGTH: 15
<212> TYPE: PRT
<213> ORGANISM: Homo sapiens

<400> SEQUENCE: 43

Arg Tyr Tyr Ser Ser Phe Val Asn Met Glu Arg Asp Leu Ala Ser
1               5                   10                  15

<210> SEQ ID NO 44
<211> LENGTH: 15
<212> TYPE: PRT
<213> ORGANISM: Homo sapiens

<400> SEQUENCE: 44

Arg Ala Glu Val Glu Asp Asn Ile Met Val Thr Phe Arg Asn Gln
1               5                   10                  15

<210> SEQ ID NO 45
<211> LENGTH: 15
<212> TYPE: PRT
<213> ORGANISM: Homo sapiens

<400> SEQUENCE: 45

Ala Glu Val Glu Asp Asn Ile Met Val Thr Phe Arg Asn Gln Ala
1               5                   10                  15

<210> SEQ ID NO 46
<211> LENGTH: 15
<212> TYPE: PRT
<213> ORGANISM: Homo sapiens
```

```
<400> SEQUENCE: 46

Glu Val Glu Asp Asn Ile Met Val Thr Phe Arg Asn Gln Ala Ser
1               5                   10                  15

<210> SEQ ID NO 47
<211> LENGTH: 15
<212> TYPE: PRT
<213> ORGANISM: Homo sapiens

<400> SEQUENCE: 47

Val Glu Asp Asn Ile Met Val Thr Phe Arg Asn Gln Ala Ser Arg
1               5                   10                  15

<210> SEQ ID NO 48
<211> LENGTH: 15
<212> TYPE: PRT
<213> ORGANISM: Homo sapiens

<400> SEQUENCE: 48

Glu Asp Asn Ile Met Val Thr Phe Arg Asn Gln Ala Ser Arg Pro
1               5                   10                  15

<210> SEQ ID NO 49
<211> LENGTH: 15
<212> TYPE: PRT
<213> ORGANISM: Homo sapiens

<400> SEQUENCE: 49

Asn Ile Met Val Thr Phe Arg Asn Gln Ala Ser Arg Pro Tyr Ser
1               5                   10                  15

<210> SEQ ID NO 50
<211> LENGTH: 15
<212> TYPE: PRT
<213> ORGANISM: Homo sapiens

<400> SEQUENCE: 50

Ile Met Val Thr Phe Arg Asn Gln Ala Ser Arg Pro Tyr Ser Phe
1               5                   10                  15

<210> SEQ ID NO 51
<211> LENGTH: 15
<212> TYPE: PRT
<213> ORGANISM: Homo sapiens

<400> SEQUENCE: 51

Met Val Thr Phe Arg Asn Gln Ala Ser Arg Pro Tyr Ser Phe Tyr
1               5                   10                  15

<210> SEQ ID NO 52
<211> LENGTH: 15
<212> TYPE: PRT
<213> ORGANISM: Homo sapiens

<400> SEQUENCE: 52

Val Thr Phe Arg Asn Gln Ala Ser Arg Pro Tyr Ser Phe Tyr Ser
1               5                   10                  15

<210> SEQ ID NO 53
<211> LENGTH: 15
<212> TYPE: PRT
<213> ORGANISM: Homo sapiens
```

```
<400> SEQUENCE: 53

Thr Phe Arg Asn Gln Ala Ser Arg Pro Tyr Ser Phe Tyr Ser Ser
1               5                   10                  15

<210> SEQ ID NO 54
<211> LENGTH: 15
<212> TYPE: PRT
<213> ORGANISM: Homo sapiens

<400> SEQUENCE: 54

Arg Gln Lys Phe Ser Ser Leu Tyr Ile Ser Gln Phe Ile Ile Met
1               5                   10                  15

<210> SEQ ID NO 55
<211> LENGTH: 15
<212> TYPE: PRT
<213> ORGANISM: Homo sapiens

<400> SEQUENCE: 55

Gln Lys Phe Ser Ser Leu Tyr Ile Ser Gln Phe Ile Ile Met Tyr
1               5                   10                  15

<210> SEQ ID NO 56
<211> LENGTH: 15
<212> TYPE: PRT
<213> ORGANISM: Homo sapiens

<400> SEQUENCE: 56

Lys Phe Ser Ser Leu Tyr Ile Ser Gln Phe Ile Ile Met Tyr Ser
1               5                   10                  15

<210> SEQ ID NO 57
<211> LENGTH: 15
<212> TYPE: PRT
<213> ORGANISM: Homo sapiens

<400> SEQUENCE: 57

Phe Ser Ser Leu Tyr Ile Ser Gln Phe Ile Ile Met Tyr Ser Leu
1               5                   10                  15

<210> SEQ ID NO 58
<211> LENGTH: 15
<212> TYPE: PRT
<213> ORGANISM: Homo sapiens

<400> SEQUENCE: 58

Ser Ser Leu Tyr Ile Ser Gln Phe Ile Ile Met Tyr Ser Leu Asp
1               5                   10                  15

<210> SEQ ID NO 59
<211> LENGTH: 15
<212> TYPE: PRT
<213> ORGANISM: Homo sapiens

<400> SEQUENCE: 59

Leu Tyr Ile Ser Gln Phe Ile Ile Met Tyr Ser Leu Asp Gly Lys
1               5                   10                  15

<210> SEQ ID NO 60
<211> LENGTH: 15
<212> TYPE: PRT
<213> ORGANISM: Homo sapiens
```

-continued

```
<400> SEQUENCE: 60

Tyr Ile Ser Gln Phe Ile Ile Met Tyr Ser Leu Asp Gly Lys Lys
1               5                   10                  15

<210> SEQ ID NO 61
<211> LENGTH: 15
<212> TYPE: PRT
<213> ORGANISM: Homo sapiens

<400> SEQUENCE: 61

Ile Ser Gln Phe Ile Ile Met Tyr Ser Leu Asp Gly Lys Lys Trp
1               5                   10                  15

<210> SEQ ID NO 62
<211> LENGTH: 15
<212> TYPE: PRT
<213> ORGANISM: Homo sapiens

<400> SEQUENCE: 62

Ser Gln Phe Ile Ile Met Tyr Ser Leu Asp Gly Lys Lys Trp Gln
1               5                   10                  15

<210> SEQ ID NO 63
<211> LENGTH: 15
<212> TYPE: PRT
<213> ORGANISM: Homo sapiens

<400> SEQUENCE: 63

Gln Phe Ile Ile Met Tyr Ser Leu Asp Gly Lys Lys Trp Gln Thr
1               5                   10                  15

<210> SEQ ID NO 64
<211> LENGTH: 15
<212> TYPE: PRT
<213> ORGANISM: Homo sapiens

<400> SEQUENCE: 64

His Asn Ile Phe Asn Pro Pro Ile Ile Ala Arg Tyr Ile Arg Leu
1               5                   10                  15

<210> SEQ ID NO 65
<211> LENGTH: 15
<212> TYPE: PRT
<213> ORGANISM: Homo sapiens

<400> SEQUENCE: 65

Asn Ile Phe Asn Pro Pro Ile Ile Ala Arg Tyr Ile Arg Leu His
1               5                   10                  15

<210> SEQ ID NO 66
<211> LENGTH: 15
<212> TYPE: PRT
<213> ORGANISM: Homo sapiens

<400> SEQUENCE: 66

Ile Phe Asn Pro Pro Ile Ile Ala Arg Tyr Ile Arg Leu His Pro
1               5                   10                  15

<210> SEQ ID NO 67
<211> LENGTH: 15
<212> TYPE: PRT
```

<400> SEQUENCE: 67

Phe Asn Pro Pro Ile Ile Ala Arg Tyr Ile Arg Leu His Pro Thr
1               5                   10                  15

<210> SEQ ID NO 68
<211> LENGTH: 15
<212> TYPE: PRT
<213> ORGANISM: Homo sapiens

<400> SEQUENCE: 68

Asn Pro Pro Ile Ile Ala Arg Tyr Ile Arg Leu His Pro Thr His
1               5                   10                  15

<210> SEQ ID NO 69
<211> LENGTH: 15
<212> TYPE: PRT
<213> ORGANISM: Homo sapiens

<400> SEQUENCE: 69

Pro Ile Ile Ala Arg Tyr Ile Arg Leu His Pro Thr His Tyr Ser
1               5                   10                  15

<210> SEQ ID NO 70
<211> LENGTH: 15
<212> TYPE: PRT
<213> ORGANISM: Homo sapiens

<400> SEQUENCE: 70

Ile Ile Ala Arg Tyr Ile Arg Leu His Pro Thr His Tyr Ser Ile
1               5                   10                  15

<210> SEQ ID NO 71
<211> LENGTH: 15
<212> TYPE: PRT
<213> ORGANISM: Homo sapiens

<400> SEQUENCE: 71

Ile Ala Arg Tyr Ile Arg Leu His Pro Thr His Tyr Ser Ile Arg
1               5                   10                  15

<210> SEQ ID NO 72
<211> LENGTH: 15
<212> TYPE: PRT
<213> ORGANISM: Homo sapiens

<400> SEQUENCE: 72

Ala Arg Tyr Ile Arg Leu His Pro Thr His Tyr Ser Ile Arg Ser
1               5                   10                  15

<210> SEQ ID NO 73
<211> LENGTH: 15
<212> TYPE: PRT
<213> ORGANISM: Homo sapiens

<400> SEQUENCE: 73

Arg Tyr Ile Arg Leu His Pro Thr His Tyr Ser Ile Arg Ser Thr
1               5                   10                  15

<210> SEQ ID NO 74
<211> LENGTH: 15
<212> TYPE: PRT
<213> ORGANISM: Homo sapiens

```
<400> SEQUENCE: 74

Pro Pro Leu Leu Thr Arg Tyr Leu Arg Ile His Pro Gln Ser Trp
1               5                   10                  15

<210> SEQ ID NO 75
<211> LENGTH: 15
<212> TYPE: PRT
<213> ORGANISM: Homo sapiens

<400> SEQUENCE: 75

Pro Leu Leu Thr Arg Tyr Leu Arg Ile His Pro Gln Ser Trp Val
1               5                   10                  15

<210> SEQ ID NO 76
<211> LENGTH: 15
<212> TYPE: PRT
<213> ORGANISM: Homo sapiens

<400> SEQUENCE: 76

Leu Leu Thr Arg Tyr Leu Arg Ile His Pro Gln Ser Trp Val His
1               5                   10                  15

<210> SEQ ID NO 77
<211> LENGTH: 15
<212> TYPE: PRT
<213> ORGANISM: Homo sapiens

<400> SEQUENCE: 77

Leu Thr Arg Tyr Leu Arg Ile His Pro Gln Ser Trp Val His Gln
1               5                   10                  15

<210> SEQ ID NO 78
<211> LENGTH: 15
<212> TYPE: PRT
<213> ORGANISM: Homo sapiens

<400> SEQUENCE: 78

Thr Arg Tyr Leu Arg Ile His Pro Gln Ser Trp Val His Gln Ile
1               5                   10                  15

<210> SEQ ID NO 79
<211> LENGTH: 15
<212> TYPE: PRT
<213> ORGANISM: Homo sapiens

<400> SEQUENCE: 79

Tyr Leu Arg Ile His Pro Gln Ser Trp Val His Gln Ile Ala Leu
1               5                   10                  15

<210> SEQ ID NO 80
<211> LENGTH: 15
<212> TYPE: PRT
<213> ORGANISM: Homo sapiens

<400> SEQUENCE: 80

Leu Arg Ile His Pro Gln Ser Trp Val His Gln Ile Ala Leu Arg
1               5                   10                  15

<210> SEQ ID NO 81
<211> LENGTH: 15
<212> TYPE: PRT
<213> ORGANISM: Homo sapiens
```

```
<400> SEQUENCE: 81

Arg Ile His Pro Gln Ser Trp Val His Gln Ile Ala Leu Arg Met
1               5                   10                  15

<210> SEQ ID NO 82
<211> LENGTH: 15
<212> TYPE: PRT
<213> ORGANISM: Homo sapiens

<400> SEQUENCE: 82

Ile His Pro Gln Ser Trp Val His Gln Ile Ala Leu Arg Met Glu
1               5                   10                  15

<210> SEQ ID NO 83
<211> LENGTH: 15
<212> TYPE: PRT
<213> ORGANISM: Homo sapiens

<400> SEQUENCE: 83

His Pro Gln Ser Trp Val His Gln Ile Ala Leu Arg Met Glu Val
1               5                   10                  15
```

MODIFIED FACTOR VIII PEPTIDES

This application is the U.S. National Stage of International Application No. PCT/GB2010/000997, filed May 17, 2010, which claims the priority benefit of Great Britain Patent Application No. 0908515.0, filed May 18, 2009.

FIELD OF THE INVENTION

The present invention relates to a peptide. In particular, it relates to peptides at least the core sequence of which is derivable from factor VIII (FVIII). The peptides can be used to reduce or prevent factor VIII inhibitor antibody formation, for example in haemophilia A treatment and acquired haemophilia.

BACKGROUND TO THE INVENTION

Haemophilia

Haemophilia belongs to a group of inheritable blood disorders that includes haemophilia A, haemophilia B (Christmas disease) and Von Willebrand's disease.

In haemophilia, the blood's ability to clot is severely reduced because an essential clotting factor is partly or completely missing, resulting in increased bleeding time. Haemophilia A is a deficiency of the clotting factor VIII, whereas Haemophilia B is a deficiency of clotting factor IX. In both diseases, the faulty gene is found on the X chromosome, so the conditions are X-linked. Haemophilia A is five times more common than haemophilia B.

Haemophilia is a lifelong inherited genetic condition, which affects females as carriers and males who inherit the condition. About a third of new diagnoses are where there is no previous family history. It appears world-wide and occurs in all racial groups. About 6,000 people are affected with haemophilia in the UK.

Haemophiliacs bleed for a prolonged period following injury. External injuries such as cuts and grazes do not usually pose serious problems: it is often possible to stop bleeding by applying a degree of pressure and covering the affected area (e.g with a plaster).

The main problem is internal bleeding into joints, muscles and soft tissues, which can occur spontaneously. Internal bleeding, such are haemorrhages into the brain, is very difficult to manage and can be fatal. Repeated bleeding in the joints causes acute pain and can cause arthritis and/or long-term joint damage leading to disability.

Treatment for haemophilia is usually by replacement of the missing clotting factor. In mild or moderate haemophilia injections may be given at the time a bleed occurs (on-demand therapy). However, in severe haemophilia regular prophylactic injections are given to help the blood to clot and minimise the likelihood of long term joint damage.

A potentially serious complication of coagulation factor replacement therapy for haemophilia A is the development of antibodies that neutralise the procoagulant function of factor VIII. Factor VIII inhibitors occur in approximately 25% of those with severe haemophilia A. Since patients with congenital haemophilia A can be genetically deficient in FVIII, the synthesis of inhibitors is an alloimmune response to the foreign protein administered to prevent or treat bleeding episodes.

CD4+ T cells play a central role in the immune response to FVIII. After being taken up by antigen-presenting cells (APCs), FVIII undergoes proteolytic degradation into peptide fragments (Reding et al (2006) Haemophilia 12(supp 6) 30-36). These peptides are then presented on the surface of the APC in association with MHC class II molecules. This complex is then recognised by the T cell receptor of a CD4+ cell specific for FVIII. In the presence of the appropriate costimulatory signals, this recognition ultimately causes the CD4+ cell to direct the synthesis of antibodies by B cells.

The incidence of inhibitor formation initially increases with the number of factor VIII treatments, but appears to plateau after 50-100 exposure days. Inhibitor formation is much more common in severe haemophilia than in moderate or mild disease and some molecular defects, most clearly large deletions and nonsense mutations in the factor VIII light chain, appear to predispose to inhibitor formation. Parameters such as the concentration, type (purified or recombinant) of replacement factor, and treatment history may also affect the likelihood of antibody production.

The management of haemophilia patients with inhibitors is an ongoing challenge. Immune tolerance induction (ITI) using a desensitization technique is successful in some patients with alloantibodies against factor VIII. This therapeutic approach requires ongoing exposure to factor replacement therapy, so is a long-term strategy.

Although ITI can be successful, a significant proportion (about 30%) of patients fail to respond to ITI. Patients with high inhibitor titres are much less likely to respond to treatment. Another significant contributing factor is age at the start of commencing ITI, with greatly decreased success rates when the patient is older than 20 (Hay et al (2005) Seminars in Thrombosis and Hemostasis 32:15-21)

When ITI therapy is unsuccessful, the inhibitor generally persists for life, and because such patients are usually high-responders, it is necessary to treat episodes of bleeding with FVIII bypassing products, such as activated prothrombin complex concentrates (FEIBA™), and recombinant-activated FVII. However, the use of such agents is associated with adverse events such as disseminated intravascular coagulation, acute myocardial infarction, pulmonary embolus and thromboses (Acharya and DiMichele (2006) Best Practice & Research Clinical Haematology 19:51-66).

Immunosuppressive therapy is sometimes used for patients who fail to response to ITI. Treatment includes administration of immunosuppressive drugs such as cyclophosphamide, prednisone, azathioprine and cyclosporine which non-specifically target the immune system. These treatments can have side-effects associated with general immunosuppression.

There is renewed interest on selective B cell depletion using Rituximab™, a humanised monoclonal antibody to B cell CD20 antigen. However, infusion reactions, serum sickness and opportunistic infections have occurred in some children treated with this drug (DiMichele (2007) J Thromb Haemost 5:143-50).

Acquired Haemophilia

Acquired haemophilia is a rare autoimmune condition which affects between 1 and 4 people in every million. In this condition, subjects who are not born with haemophilia develop antibodies against one of the clotting factors such as factor VIII. It is thought that pregnancy and autoimmune diseases such as rheumatoid arthritis and cancer may increase the risk of developing acquired haemophilia. Although there are differences in the underlying immune mechanisms leading to their production, the clinical manifestations of FVIII inhibitors produced in response to coagulation factor replacement therapy and those produced in acquired haemophilia are similar.

Acquired haemophiliac patients have a mortality rate that approaches 25%, partly because of the association of acquired inhibitors with severe bleeding complications. The therapy of acquired autoantibody inhibitors is based primarily on the need to control or prevent acute hemorrhagic complications, which frequently are life and limb threatening and secondarily to eradicate the autoantibody to restore normal coagulation.

Some bleeds associated with low titre autoantibody inhibitors (<5 Bethesda Units) may be treated effectively with FVIII concentrates administered at high doses. Porcine FVIII concentrate was formerly considered a critical first-line therapy for acquired hemophilia-related bleeding since it was the only replacement therapy that provided an opportunity to actually measure post-infusion FVIII coagulation activity levels in the laboratory. The product was removed from the marketplace in 2004 because of contamination of the porcine plasma pools by porcine parvovirus. Now, "bypassing" agents are most commonly used, but potential risks of thrombogenicity exist and there is only about 80% efficacy for each product. Plasma exchange via plasmapheresis and extracorporeal immunoadsorption may be necessary to temporarily reduce the inhibitor titer enough for bypassing agents or FVIII replacement to provide adequate hemostasis.

Eradication of autoantibody inhibitors depends on immunosuppressive measures, such as: (1) administration of corticosteroids with 30%-50% efficacy in 3-6 weeks; (2) use of cytotoxic and myelosuppressive chemotherapeutic agents, e.g., cyclophosphamide, cyclosporine, 2-chlorodeoxyadenosine; (3) immunomodulation with intravenous immunoglobulin; and (4) selective B-lymphocyte depletion with rituximab. Rituximab™ responders may require concurrent use of steroids and relapses may respond to retreatment.

Thus, all currently available methods for reducing alloantibody production associated with haemophilia A treatment, and autoantibody production in acquired haemophilia, have shortcomings. There is therefore a need for improved methods to address the issue of anti-FVIII antibodies in haemophilia A and acquired haemophilia.

The present inventors have found that it is possible to prevent FVIII inhibitor antibody formation by pre-tolerising the patient with FVIII-derived peptides.

SUMMARY OF ASPECTS OF THE INVENTION

The first aspect of the present invention, therefore, relates to a peptide, at least part of the sequence of which is derivable from FVIII, which is capable of inducing or restoring tolerance to FVIII.

In a first embodiment, the present invention provides a peptide comprising one of the following FVIII-derived sequences:

| Sequence | SEQ ID NO: |
|---|---|
| GTLMVFFGNVDSSGI | 13 |
| TQTLHKFILLFAVFD | 2 |
| SLYISQFIIMYSLDG | 3 |
| PPIIARYIRLHPTHY | 4 |
| PPLLTRYLRIHPQSW | 5 |
| MHTVNGYVNRSLPGL | 6 |
| LGQFLLFCHISSHQH | 7 |
| DTLLIIFKNQASRPY | 8 |
| PRCLTRYYSSFVNME | 9 |
| TENIQRFLPNPAGVQ | 10 |
| DNIMVTFRNQASRPY | 11 |
| RYLRIHPQSWVHQIA | 12 | with one or more of the following modifications:
(i) removal of one or more hydrophobic amino acid(s);
(ii) replacement of one or more hydrophobic amino acid(s) with charged hydrophilic amino acid(s); and
(iii) insertion of a charged amino acid at one or both terminus (i)

which modified peptide is capable of binding to an MHC class II molecule without further antigen processing and being recognised by a factor VIII specific T cell.

The "parent" (unmodified) peptide may be PRCLTRYYSSFVNME (SEQ ID NO: 9) or DNIMVTFRNQASRPY (SEQ ID NO: 11).

In a second embodiment the present invention provides a peptide comprising the sequence
X(aa)n-core sequence -(aa)m
wherein X is a charged hydrophilic residue;
aa is an amino acid;
n is an integer between 0 and 5;
m is an integer between 0 and 5; and
the "core sequence" is selected from the following group of FVIII-derived peptides:

| | |
|---|---|
| LYISQFIIM | (SEQ ID NO: 14) |
| FIIMYSLDG | (SEQ ID NO: 15) |
| IARYIRLHP | (SEQ ID NO: 16) |
| LIIFKNQAS | (SEQ ID NO: 17) |
| LTRYYSSFV | (SEQ ID NO: 18) |
| MVTFRNQAS | (SEQ ID NO: 19) |
| LRIHPQSWV | (SEQ ID NO: 20) | which peptide is capable of binding to an MHC class II molecule without further antigen processing and being recognised by a factor VIII specific T cell.

For example, the peptide may comprise the sequence

| | |
|---|---|
| XDNIMVTFRNQAS | (SEQ ID NO: 21). |

In a third embodiment, the present invention provides a peptide comprising the sequence:
Y(aa)n-core sequence-(aa)mZ
wherein Y and Z are charged amino acids having reverse polarity;
aa is an amino acid;
n is an integer between 0 and 5;
m is an integer between 0 and 5; and
the "core sequence" is selected from the following group of FVIII-derived peptides:

| | |
|---|---|
| LYISQFIIM | (SEQ ID NO: 14) |
| FIIMYSLDG | (SEQ ID NO: 15) |
| IARYIRLHP | (SEQ ID NO: 16) |
| LIIFKNQAS | (SEQ ID NO: 17) |
| LTRYYSSFV | (SEQ ID NO: 18) |
| MVTFRNQAS | (SEQ ID NO: 19) |
| LRIHPQSWV | (SEQ ID NO: 20) | which peptide is capable of binding to an MHC class II molecule without further antigen processing and being recognised by a factor VIII specific T cell.

For example, the peptide may comprise the sequence:

YDNIMVTFRNQASZ (SEQ ID NO: 22)

In the third embodiment, for example, Y may be a positively charged amino acid and Z may be a negatively charged amino acid. Alternatively, Y may be a negatively charged amino acid and Z may be a positively charged amino acid.

A charged, hydrophilic amino acid may, for example be D, E, K, H or R. A positively charged amino acid may, for example be K, H or R. A negatively charged amino acid may, for example be D or E.

The peptide of the first aspect of the invention may, for example, comprise or consist of the sequence EDNIMVT-FRNQASR (SEQ ID NO: 23).

In a second aspect, the present invention provides a composition, such as a pharmaceutical composition comprising one or more peptide(s) of the first aspect of the invention. The composition may comprise a plurality of peptides wholly or partly derivable from FVIII which are capable of inducing or restoring tolerance to FVIII.

The composition may be in the form of a kit, in which the plurality of peptides are provided separately for separate, subsequent, sequential or simultaneous administration.

The peptide or a composition of the invention may be for use in suppressing, reducing, or preventing the development of factor VIII inhibitor antibodies.

The present invention also provides the use of such a peptide or composition in the manufacture of a medicament to suppress, reduce or prevent the development of factor VIII inhibitor antibodies.

The present invention also provides a method for suppressing, preventing or reducing the development of Factor VIII inhibitor antibodies in a subject, which comprises the step of administration of such a peptide or composition to the subject.

The subject may be deficient in FVIII. In particular the subject may have haemophilia A, and may be, or be about to, undergo factor VIII replacement therapy.

Alternatively the subject may have, or be at risk from contracting, acquired haemophilia.

Factor VIII inhibitors are found more frequently in individuals expressing HLA-DR2. The subject treated by the method of the invention may therefore be HLA-DR2 positive.

DETAILED DESCRIPTION

Peptide

Figure 1:
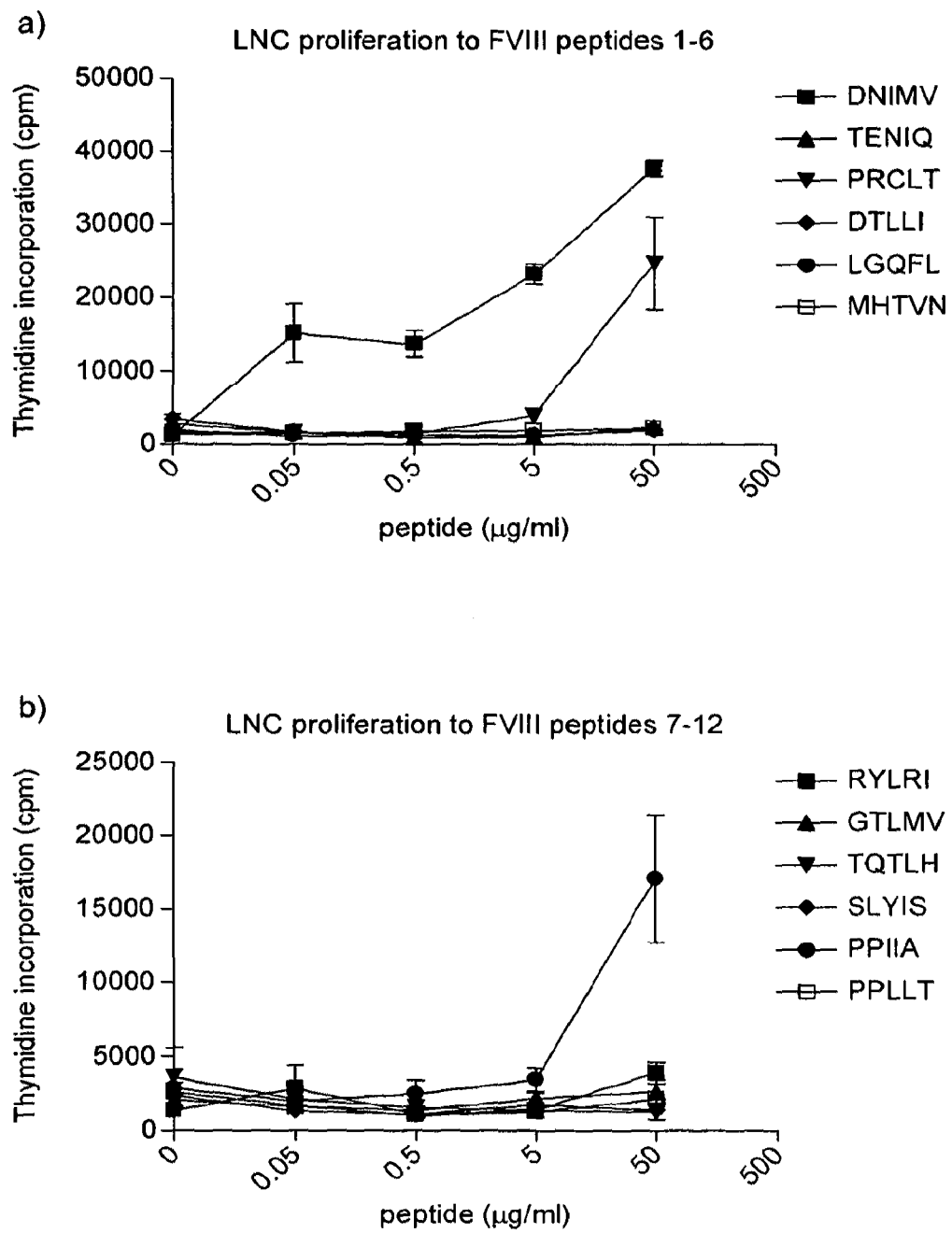
FIG. 1: Recall responses for lymph node cells (LNC) from FVIII+DR2+ mice primed with rhFVIII/CFA
 a) LNC proliferation to FVIII peptides 1-6
 b) LNC proliferation to FVIII peptides 7-12
 c) LNC proliferation to FVIII peptides 1, 3 and 11
Figure 1:
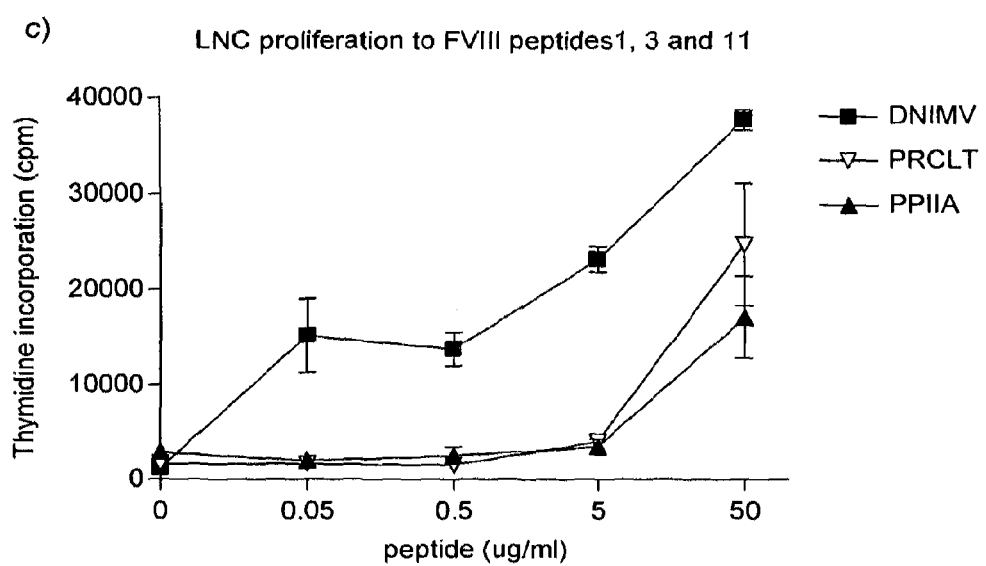

The present invention relates to a peptide.

The term "peptide" is used in the normal sense to mean a series of residues, typically L-amino acids, connected one to the other typically by peptide bonds between the α-amino and carboxyl groups of adjacent amino acids. The term includes modified peptides and synthetic peptide analogues.

The peptide of the present invention may be made using chemical methods (Peptide Chemistry, A practical Textbook. Mikos Bodansky, Springer-Verlag, Berlin.). For example, peptides can be synthesized by solid phase techniques (Roberge J Y et al (1995) Science 269: 202-204), cleaved from the resin, and purified by preparative high performance liquid chromatography (e.g., Creighton (1983) Proteins Structures And Molecular Principles, WH Freeman and Co, New York N.Y.). Automated synthesis may be achieved, for example, using the ABI 43 1 A Peptide Synthesizer (Perkin Elmer) in accordance with the instructions provided by the manufacturer.

The peptide may alternatively be made by recombinant means, or by cleavage of to peptide from factor VIII followed by modification of one or both ends. The composition of a peptide may be confirmed by amino acid analysis or sequencing (e.g., the Edman degradation procedure).

For practical purposes, there are various other characteristics which the peptide may show. For example, it is important that the peptide is sufficiently stable in vivo to be therapeutically useful. The half-life of the peptide in vivo may be at least 10 minutes, 30 minutes, 4 hours, or 24 hours.

The peptide may also demonstrate good bioavailability in vivo. The peptide may maintain a conformation in vivo which enables it to bind to an MHC molecule at the cell surface without due hindrance.

Core Residues

In an adaptive immune response, T lymphocytes are capable of recognising internal epitopes of a protein antigen. Antigen presenting cells (APC) take up protein antigens and degrade them into short peptide fragments. A peptide may bind to a major histocompatibility complex (MHC) class I or II molecule inside the cell and be carried to the cell surface. When presented at the cell surface in conjunction with an MHC molecule, the peptide may be recognised by a T cell (via the T cell receptor (TCR)), in which case the peptide is a T cell epitope.

An epitope is thus a peptide derivable from an antigen which is capable of binding to the peptide-binding groove of a MHC class I or II molecule and be recognised by a T cell.

The minimal epitope is the shortest fragment derivable from an epitope, which is capable of binding to the peptide-binding groove of a MHC class I or II molecule and being recognised by a T cell. For a given immunogenic region, it is typically possible to generate a "nested set" of overlapping peptides which act as epitopes, all of which contain the minimal epitope but differ in their flanking regions.

By the same token, it is possible to identify the minimal epitope for a particular MHC molecule:T cell combination by measuring the response to truncated peptides. For example if a response is obtained to the peptide comprising residues 1-15 in the overlapping library, sets which are truncated at both ends (i.e. 1-14, 1-13, 1-12 etc. and 2-15, 3-15, 4-15 etc.) can be used to identify the minimal epitope.

The present invention provides peptides comprising a "core residue" sequence of FVIII which selected from the following list:

| | |
|---|---|
| LYISQFIIM | (SEQ ID NO: 14) |
| FIIMYSLDG | (SEQ ID NO: 15) |
| IARYIRLHP | (SEQ ID NO: 16) |
| LIIFKNQAS | (SEQ ID NO: 17) |
| LTRYYSSFV | (SEQ ID NO: 18) |
| MVTFRNQAS | (SEQ ID NO: 19) |
| LRIHPQSWV | (SEQ ID NO: 20) |

These core residue sequences were predicted using HLA-DR2 binding algorithms to represent or comprise the minimal epitope for each region, as shown in the Examples.

Apitopes

The present inventors have previously determined that there is a link between the capacity of a peptide to bind to an MHC class I or II molecule and be presented to a T cell without further antigen processing, and the peptide's capacity to induce tolerance in vivo (WO 02/16410). If a peptide is too long to bind the peptide binding groove of an MHC molecule without further processing (e.g. trimming), or binds in an inappropriate conformation then it will not be tolerogenic in vivo. If, on the other hand, the peptide is of an appropriate size and conformation to bind directly to the MHC peptide binding groove and be presented to a T cell, then this peptide can be predicted to be useful for tolerance induction.

It is thus possible to investigate the tolerogenic capacity of a peptide by investigating whether it can bind to an MHC class I or II molecule and be presented to a T cell without further antigen processing in vitro.

The peptides of the present invention are apitopes (Antigen Processing-Indepent epiTOPES) in that they are capable of binding to an MHC class II molecule and stimulating a response from factor VIII specific T cells without further antigen processing. Such apitopes can be predicted to cause tolerance to FVIII, following the rule-based method described in WO 02/16410.

A peptide of the present invention may be any length that is capable of binding to an MHC class I or II molecule without further processing. Typically, the peptide of the present invention is capable of binding MHC class II.

Peptides that bind to MHC class I molecules are typically 7 to 13, more usually 8 to 10 amino acids in length. The binding of the peptide is stabilised at its two ends by contacts between atoms in the main chain of the peptide and invariant sites in the peptide-binding groove of all MHC class I molecules. There are invariant sites at both ends of the groove which bind the amino and carboxy termini of the peptide. Variations is peptide length are accommodated by a kinking in the peptide backbone, often at proline or glycine residues that allow the required flexibility.

Peptides which bind to MHC class II molecules are typically between 8 and 20 amino acids in length, more usually between 10 and 17 amino acids in length, and can be longer (for example up to 40 amino acids). These peptides lie in an extended conformation along the MHC II peptide-binding groove which (unlike the MHC class I peptide-binding groove) is open at both ends. The peptide is held in place mainly by main-chain atom contacts with conserved residues that line the peptide-binding groove.

Peptide Sequences

The first embodiment of the invention relates to a peptide comprising one of the following FVIII-derived sequences:

GTLMVFFGNVDSSGI

TQTLHKFILLFAVFD

SLYISQFIIMYSLDG

PPIIARYIRLHPTHY

PPLLTRYLRIHPQSW

MHTVNGYVNRSLPGL

LGQFLLFCHISSHQH

DTLLIIFKNQASRPY

PRCLTRYYSSFVNME

TENIQRFLPNPAGVQ

DNIMVTFRNQASRPY

RYLRIHPQSWVHQIA with one or more of the following modifications:

(i) removal of one or more hydrophobic amino acid(s);

(ii) replacement of one or more hydrophobic amino acid(s) with charged hydrophilic amino acid(s); and (iii) insertion of a charged amino acid at one or both terminus(i)

which modified peptide is capable of binding to an MHC class II molecule without further antigen processing and being recognised by a factor VIII specific T cell.

A list of standard amino acids, together with their side chain polarity, charge and hydropathy index is given in Table 1.

TABLE 1

| Amino Acid | 3-Letter | 1-Letter | Side chain polarity | Side chain charge (pH 7) | Hydropathy index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

Hydrophobic amino acids include: G, C, M, A, P, I, L, V and the aromatic amino acids F and W. Hydrophobic amino acids may be removed from the ends of the sequence or within the sequence.

Charged hydrophilic amino acids include: K, R, D, H and E. Hydrophobic amino acids may be exchanged with charged hydrophilic amino acids the ends of the sequence or within the sequence.

One or more charged amino acid(s) may be inserted at the N-terminus of the sequence. Advantageously, a positively charged amino acid is inserted or substituted at one terminus and a negatively charged amino acid is inserted/substituted at the other terminus in order to create a charge dipole.

Modification of the parent sequence should not significantly impair binding of the peptide to the peptide binding groove of an MHC molecule, its capacity to be recognised by a T cell, or its capacity to act as an apitope (bind to an MHC molecule and be presented to a T cell without further antigen processing). This may be readily tested using known antigen presentation assays and T-cell hybridomas.

The second embodiment of the invention relates to a peptide comprising the sequence $X(aa)_a$-core sequence $-(aa)_m$ wherein X is a charged hydrophilic residue;

aa is an amino acid;

n is an integer between 0 and 5;

m is an integer between 0 and 5; and the "core sequence" is selected from the following group of FVIII-derived peptides:

```
LYISQFIIM

FIIMYSLDG

IARYIRLHP

LIIFKNQAS

LTRYYSSFV

MVTFRNQAS

LRIHPQSWV
``` which peptide is capable of binding to an MHC class II molecule without further antigen processing and being recognised by a factor VIII specific T cell.

The sequence $(aa)_n$ or $(aa)_m$ can be any sequence of between 4 and 5 amino acids. For example, the peptide may have the sequence:

```
XDNIMVTFRNQAS
``` in which case, n=3 and m=0.

The third embodiment of the present invention relates to a peptide comprising the sequence:

$Y(aa)_a$-core sequence-$(aa)_m Z$ wherein Y and Z are charged amino acids having reverse polarity;

aa is an amino acid;

n is an integer between 0 and 5;

m is an integer between 0 and 5; and the "core sequence" is selected from the following group of FVIII-derived peptides:

```
LYISQFIIM

FIIMYSLDG
```

-continued

```
IARYIRLHP

LIIFKNQAS

LTRYYSSFV

MVTFRNQAS

LRIHPQSWV
``` which peptide is capable of binding to an MHC class II molecule without further antigen processing and being recognised by a factor VIII specific T cell.

For example, for the peptide EDNIMVTFRNQASR (SEQ ID NO: 23),

Y=E;

$(aa)_n$=DNI m=0; and

Z=R

The peptide may comprise the core residue sequence, together with additional flanking sequences at the N and/or C terminal end ($(aa)_n$ and $(aa)_m$ respectively), provided that the resulting peptide is capable of binding to an MHC class II molecule without further antigen processing.

The flanking N and/or C terminal sequences may be derivable from the sequences flanking the core residue sequences in human FVIII.

APIPS

Various antigen processing independent presentation systems (APIPS) are known, including:

a) fixed APC (with or without antibodies to CD28);

b) Lipid membranes containing Class I or II MHC molecules (with or without antibodies to CD28); and c) purified natural or recombinant MHC in plate-bound form (with or without antibodies to CD28).

All of these systems are capable of presenting antigen in conjunction with an MHC molecule, but are incapable of processing antigen. In all these systems the processing function is either absent or disabled. This makes it possible to investigate whether a peptide can bind to an MHC class I or II molecule and be presented to a T cell without further antigen processing.

The use of fixed APC to investigate T cell responses is well known in the art, for example in studies to investigate the minimal epitope within a polypeptide, by measuring the response to truncated peptides (Fairchild et al (1996) Int. Immunol. 8:1035-1043). APC may be fixed using, for example formaldehyde (usually paraformaldehyde) or glutaraldehyde.

Lipid membranes (which may be planar membranes or liposomes) may be prepared using artificial lipids or may be plasma membrane/microsomal fractions from APC.

In use, the APIPS may be applied to the wells of a tissue culture plate. Peptide antigens are then added and binding of the peptide to the MHC portion of the APIPS is detected by addition of selected T cell lines or clones. Activation of the T cell line or clone may be measured by any of the methods known in the art, for example via $^{3}H$-thymidine incorporation or cytokine secretion.

Factor VIII

The core sequence of peptide of the invention is derivable from factor VIII. One or both flanking sequences ($(aa)_n$ and $(aa)_m$) may also be derivable from factor VIII.

Factor VIII participates in the intrinsic pathway of blood coagulation; factor VIII is a cofactor for factor IXa which, in the presence of Ca+2 and phospholipids, converts factor X to the activated form Xa.

The factor VIII gene produces two alternatively spliced transcripts. Transcript variant 1 encodes a large glycoprotein, isoform a, which circulates in plasma and associates with von Willebrand factor in a noncovalent complex. This protein undergoes multiple cleavage events. Transcript variant 2 encodes a putative small protein, isoform b, which consists primarily of the phospholipid binding domain of factor VIIIc. This binding domain is essential for coagulant activity.

The complete 186,000 base-pair sequence of the human factor VIII gene was elucidated in the mid 1980s (Gitschier et al (1984) Nature 312 326-330). At the same time, DNA clones encoding the complete 2351 amino acid sequence were used to produce biologically active factor VIII in cultured mammalian cells (Wood et al (1984) Nature 312:330-337). The complete 2,351 amino acid sequence for human factor VIII is given in SEQ ID No. 1.

The core residues of peptide of the present invention are derivable from factor VIII. Optionally the flanking sequence(s) may also be derivable from factor VIII if they are the same as the sequences flanking the core sequence in the native FVIII polypeptide. This sequence may be obtainable or obtained from cleavage of the factor VIII sequence.

Solubility

The peptide of the first embodiment of the invention is a modified form of one of the following peptides:

```
GTLMVFFGNVDSSGI
TQTLHKFILLFAVFD
SLYISQFIIMYSLDG
PPIIARYIRLHPTHY
PPLLTRYLRIHPQSW
MHTVNGYVNRSLPGL
LGQFLLFCHISSHQH
DTLLIIFKNQASRPY
PRCLTRYYSSFVNME
TENIQRFLPNPAGVQ
DNIMVTFRNQASRPY
RYLRIHPQSWVHQIA
```

These peptides have already been shown to act as apitopes and be tolerogenic in vivo (see examples and International patent application No PCT/GB2008/003996).

It has since come to light that solubility is an important consideration in peptide-mediated tolerance induction. Solubility may be improved by one or more of the following:

(i) removal of one or more hydrophobic residues;

(ii) addition/substitution to add one or more charged hydrophilic residues (iii) placing positively and negatively charged amino acids at either end to create a charge dipole.

The modified peptide may be more soluble that the parent (unmodified) peptide. The modified peptide may have 2, 3, 4, or 5-fold greater solubility than the parent peptide. The peptide may be soluble at concentrations of up to 0.5 mg/ml, 1 mg/ml, or 5 mg/ml.

Tolerance

T cell epitopes play a central role in the adaptive immune response to any antigen, whether self or foreign. The central role played by T cell epitopes in hypersensitivity diseases (which include allergy, autoimmune diseases and transplant rejection) has been demonstrated through the use of experimental models. It is possible to induce inflammatory or allergic diseases by injection of synthetic peptides (based on the structure of T cell epitopes) in combination with adjuvant.

By contrast, it has been shown to be possible to induce immunological tolerance towards particular antigens by administration of peptide epitopes in soluble form. Administration of soluble peptide antigens has been demonstrated as an effective means of inhibiting disease in experimental autoimmune encephalomyelitis (EAE—a model for multiple sclerosis (MS)) (Metzler and Wraith (1993) Int. Immunol. 5:1159-1165; Liu and Wraith (1995) Int. Immunol. 7:1255-1263; Anderton and Wraith (1998) Eur. J. Immunol. 28:1251-1261); and experimental models of arthritis, diabetes, and uveoretinitis (reviewed in Anderton and Wraith (1998) as above). This has also been demonstrated as a means of treating an ongoing disease in EAE (Anderton and Wraith (1998) as above).

Tolerance is the failure to respond to an antigen. Tolerance to self antigens is an essential feature of the immune system, when this is lost, autoimmune disease can result. The adaptive immune system must maintain the capacity to respond to an enormous variety of infectious agents while avoiding autoimmune attack of the self antigens contained within its own tissues. This is controlled to a large extent by the sensitivity of immature T lymphocytes to apoptotic cell death in the thymus (central tolerance). However, not all self antigens are detected in the thymus, so death of self-reactive thymocytes remains incomplete. There are thus also mechanisms by which tolerance may be acquired by mature self-reactive T lymphocytes in the peripheral tissues (peripheral tolerance). A review of the mechanisms of central and peripheral tolerance is given in Anderton et al (1999) (*Immunological Reviews* 169:123-137).

In haemophilia A, patients have a defect in the factor VIII gene. This means that factor VIII is not recognised as a "self" antigen by the immune system. When factor VIII is administered during coagulation factor replacement therapy, therefore, an alloimmune response is generated to the foreign protein, leading to the production of FVIII inhibitor antibodies.

The peptides of the present invention are capable of inducing tolerance to factor VIII such that when FVIII is administered therapeutically, it does not induce an immune response and FVIII inhibitors do not develop.

Acquired haemophilia is an autoimmune disease in which tolerance to factor VIII breaks down. In this case, peptides of the present invention may be administered to reinstate tolerance to this self protein and curtail the pathogenic immune response.

Tolerance may result from or be characterised by the induction of anergy in at least a portion of CD4+ T cells. In order to activate a T cell, a peptide must associate with a "professional" APC capable of delivering two signals to T cells. The first signal (signal 1) is delivered by the MHC-peptide complex on the cell surface of the APC and is received by the T cell via the TCR. The second signal (signal 2) is delivered by costimulatory molecules on the surface of the APC, such as CD80 and CD86, and received by CD28 on the surface of the T cell. It is thought that when a T cell receives signal 1 in the absence of signal 2, it is not activated and, in fact, becomes anergic. Anergic T cells are refractory to subsequent antigenic challenge, and may be capable of suppressing other immune responses. Anergic T cells are thought to be involved in mediating T cell tolerance.

Without wishing to be bound by theory, the present inventors predict that peptides which require processing before they can be presented in conjunction with MHC molecules do not induce tolerance because they have to be handled by mature antigen presenting cells. Mature antigen presenting cells (such as macrophages, B cells and dendritic cells) are capable of antigen processing, but also of delivering both signals 1 and 2 to a T cell, leading to T cell activation. Apitopes, on the other hand, will be able to bind class II MHC on immature APC. Thus they will be presented to T cells without costimulation, leading to T cell anergy and tolerance.

Of course, apitopes are also capable of binding to MHC molecules at the cell surface of mature APC. However, the immune system contains a greater abundance of immature than mature APC (it has been suggested that less than 10% of dendritic cells are activated, Summers et al. (2001) Am. J. Pathol. 159: 285-295). The default position to an apitope will therefore be anergy/tolerance, rather than activation.

The induction of tolerance to FVIII can be monitored in vivo by looking for a reduction in the level of:
(i) FVIII inhibitory antibodies:
(ii) CD4+ T cells specific for FVIII
(iii) B cells capable of secreting FVIII inhibitory antibodies by techniques known in the art.

It has been shown that, when tolerance is induced by peptide administration, the capacity of antigen-specific CD4+ T cells to proliferate is reduced. Also, the production of IL-2, IFN-γ and IL-4 production by these cells is down-regulated, but production of IL-10 is increased. Neutralisation of IL-10 in mice in a state of peptide-induced tolerance has been shown to restore completely susceptibility to disease. It has been proposed that a population of regulatory cells persist in the tolerant state which produce IL-10 and mediate immune regulation (Burkhart et al (1999) Int. Immunol. 11:1625-1634).

The induction of tolerance can therefore also be monitored by various techniques including:

(a) the induction of anergy in CD4+ T cells (which can be detected by subsequent challenge with FVIII in vitro);

(b) changes in the CD4+ T cell population, including (i) reduction in proliferation;

(ii) down-regulation in the production of IL-2, IFN-γ and IL-4; and (iii) increase in the production of IL-10.

As used herein, the term "tolerogenic" means capable of inducing tolerance.

Composition

The present invention also relates to a composition, such as a pharmaceutical composition comprising one or more peptide(s) according to the invention.

The peptide may comprise a plurality of peptides, for example, two, three, four, five or six peptides.

The composition of the present invention may be for prophylactic or therapeutic use.

When administered for prophylactic use, the composition may reduce or prevent the generation of an immune response to FVIII. The level of immune response is less than would have been obtained in the patient had not been treated with the composition. The term "reduce" indicates that a partial reduction in immune response is observed, such as a 50%, 70%, 80% or 90% reduction in the response that would have been observed in the patient had not been treated with the composition (or in the response observed in an untreated patient over the same time-frame). The term "prevent" indicates that no appreciable immune response to FVIII is observed.

When administered for therapeutic use, the composition may suppress an already ongoing immune response to FVIII. The term "suppress" indicates a reduction in the level of an on-going immune response, compared to the level before peptide treatment, or the level which would have been observed at the same time point had the treatment not been given.

Treatment with the composition of the present invention may cause a reduction in levels of any or all of the following:

(i) FVIII inhibitory antibodies:

(ii) CD4+ T cells specific for FVIII (iii) B cells secreting FVIII inhibitory antibodies.

Detection of all these factors can be carried out by techniques known in the art, such as ELISA, FACS etc.

Treatment with the composition of the present invention may also or alternatively cause anergy in CD4+ T cells specific for FVIII. Anergy can be detected by for example subsequent challenge with FVIII in vitro.

It is important to bear in mind that not all immune responses to FVIII are pathogenic. Non-inhibitory anti-FVIII antibodies may be found in haemophilia patients without inhibitors (Moreau et al (2000) Blood 95:3435-41) and approximately 15% of healthy blood donors (Algiman et al (1992) 89:3795-9).

FVIII inhibitors may be detected by the Nijmegen modification of the clotting Bethesda assay, in which the ability of the patient's plasma to inactivate FVIII in normal plasma is tested. A Bethesda unit is defined as the amount of antibody that neutralizes 50% of plasma FVIII activity, and titres of 0.6 BU or greater suggest the presence of antibody.

Inhibitors are generally classified as low titre if the level is $<5$ BU and high titre if $\geq 5$ BU.

The level of circulating FVIII inhibitory antibodies may be reduced to 90%, 75%, 50%, 20%, 10% 5% of the level of antibodies which would have been observed had the patient not received treatment.

The level of circulating FVIII inhibitory antibodies may be reduced to 5, 4, 3, 2, 1 or 0.5 BU.

The peptides and composition of the invention may increase the amount or proportion of therapeutically administered FVIII which is available to aid clotting in a patient. This is due to the reduction in FVIII inhibitors which may effectively remove a proportion of FVIII from exerting its therapeutic function. The peptide or composition of the invention may increase the amount of available FVIII by, for example, 10%, 25%, 50% 75% or 100%.

The peptides and composition of the invention may thus reduce the amount of FVIII which needs to be administered to aid clotting in a patient.

Formulation

The composition may by prepared as an injectable, either as liquid solution or suspension; solid form suitable for solution in, or suspension in, liquid prior to injection may also be prepared. The preparation may also be emulsified, or the peptides encapsulated in liposomes. The active ingredients may be mixed with excipients which are pharmaceutically acceptable and compatible with the active ingredient. Suitable excipients are, for example, water, saline (for example, phosphate-buffered saline), dextrose, glycerol, ethanol, or the like and combinations thereof.

In addition, if desired, the composition may contain minor amounts of auxiliary substances such as wetting or emulsifying agents and/or pH buffering agents. Buffering salts include phosphate, citrate, acetate. Hydrochloric acid and/or sodium hydroxide may be used for pH adjustment. For stabilisation, disaccharides may be used such as sucrose or trehalose.

If the composition comprises a plurality of peptides, the relative ratio of the peptides may be approximately equal. Alternatively the relative ratios of each peptide may be altered, for example, to focus the tolerogenic response on a particular sub-set of autoreactive T-cells or if it is found that one peptide works better than the others in particular HLA types.

After formulation, the composition may be incorporated into a sterile container which is then sealed and stored at a low temperature, for example 4° C., or it may be freeze-dried.

Conveniently the composition is prepared as a lyophilized (freeze dried) powder. Lyophilisation permits long-term storage in a stabilised form. Lyophilisation procedures are well known in the art, see for example http colon-slash-slash www.devicelink.com/ivdt/archive/97/01/006.html. Bulking agents are commonly used prior to freeze-drying, such as mannitol, dextran or glycine.

The composition may be administered in a convenient manner such as by the oral, intravenous (where water soluble), intramuscular, subcutaneous, sublingual, intranasal, intradermal or suppository routes or implanting (e.g. using slow release molecules).

The composition may advantageously be administered via intranasal, subcutaneous or intradermal routes.

The peptide and composition of the invention may be used to treat a human subject. The subject may have haemolphilia A, in particular severe haemophilia A. The subject may be genetically deficient in FVIII. The subject may have acquired haemophilia. The subject may have inhibitory anti-FVIII antibodies.

The subject may be undergoing or about to undergo coagulant replacement therapy with FVIII.

The subject may be undergoing or about to undergo gene therapy with the FVIII gene.

The subject may be an HLA-haplotype which is associated with a predisposition to develop inhibitory anti-FVIII alloantibodies or autoantibodies. The subject may express HLA-DR2. Methods for determining the HLA haplotype of an individual are known in the art.

Typically, a physician will determine the actual dosage which will be most suitable for an individual subject and it will vary with the age, weight and response of the particular patient.

In a preferred embodiment a "dose escalation" protocol may be followed, where a plurality of doses is given to the patient in ascending concentrations. Such an approach has been used, for example, for phospholipase A2 peptides in immunotherapeutic applications against bee venom allergy (Müller et al (1998) J. Allergy Clin Immunol. 101:747-754 and Akdis et al (1998) J. Clin. Invest. 102:98-106).

Kits

Conveniently, if the composition comprises a plurality of peptides, they may be administered together, in the form of a mixed composition or cocktail. However, there may be circumstances in which it is preferable to provide the peptides separately in the form of a kit, for simultaneous, separate, sequential or combined administration.

The kit may also comprise mixing and/or administration means (for example a vapouriser for intranasal administration; or a syringe and needle for subcutaneous/intradermal dosing). The kit may also comprise instructions for use.

The pharmaceutical composition or kit of the invention may be used to treat and/or prevent a disease.

In particular, the composition/kit may be used to treat and/or prevent haemophilia A or acquired haemophilia.

Haemophilia A

Hemophilia A (classic hemophilia), is caused by the deficiency of Factor VIII.

Hemophilia A has an estimated incidence of 1 in 10,000 males, while hemophilia B is estimated to occur in one in 40,000 males. Approximately 1 woman in 5,000 is a carrier for hemophilia A, and 1 in 20,000 is a carrier of hemophilia B.

Hemophilia is typically divided into three classes: severe, moderate and mild, based on the level of clotting factor in the blood. In severe hemophilia, there is less than 1 percent of normal clotting factor. The degree of severity tends to be consistent from generation to generation.

Contrary to popular belief, minor cuts and wounds do not usually present a threat to hemophiliacs. Rather, the greatest danger comes from spontaneous bleeding that may occur in joints and muscles. This is most prone to occur during years of rapid growth, typically between the ages of 5 and 15 years.

Repeated spontaneous bleeding in joints may cause arthritis, and adjacent muscles become weakened. Pressure on nerves caused by the accumulation of blood may result in pain, numbness, and temporary inability to move the affected area.

Haemophilia A is usually diagnosed with a blood test to determine the effectiveness of clotting and to investigate whether the levels of clotting factors are abnormal.

The development of purified clotting factors in the 1970s, isolated from donated blood, significantly improved the long-term outlook for hemophiliacs. Mild to moderate haemophiliacs can use treatment with FVIII on an ad hoc basis, whereas severe haemophiliacs may require regular, indefinite treatment.

Previously, patients were given factor VIII concentrates pooled from thousands of plasma donations. This lead to significant problems of contamination with viral pathogens, particularly the human immunodeficiency virus and the hepatitis viruses. Monoclonal antibody purification techniques, heat inactivation, and virucidal detergent treatments have rendered plasma-derived concentrates relatively safe.

Recombinant DNA technology has now provided a series of synthetic products, such as Recombinate™ (antihemophilic factor (recombinant)) and Kogenate™ (antihemophilic factor (recombinant)). Kogenate™ is made using baby hamster kidney cells expressing human factor VIII. The resulting factor is highly purified, eliminating any possibility of transmission of virus from plasma.

The peptide or composition of the present invention may be administered before and/or during factor VIII replacement therapy.

Hemophilia A is an ideal disease target for gene therapy since i) it is caused by a mutations in a single identified gene, ii) a slight increase in clotting factor levels in vivo can convert severe hemophilia into milder disease, and iii) current replacement therapies are considered suboptimal. Also, there is a wide range of safety if there is an "overshoot" of desired level of coagulation activity.

Unfortunately, to date the promise of gene therapy as a cure for haemophilia has not been realized, primarily because of difficulties in finding a gene delivery system which is sufficiently non-immunogenic to allow for long term expression of the clotting factor.

The peptides of the present invention would also be suitable for tolerising a subject prior to gene therapy with factor VIII and/or managing FVIII inhibitor formation in a patient following gene therapy.

Acquired Haemophilia

Acquired haemophilia is characterised by the presence of autoantibody inhibitors against FVIII in individuals with previously normal coagulation. It is a rare condition, with an estimated incidence of 1-3 per million population per year. The mortality rate associated with acquired autoantibody inhibitors approaches 25% versus the substantially lower risk of death in those with alloantibodies.

Compared to alloantibody inhibitor patients, acquired hemophilia is characterized by: (1) a more severe bleeding pattern; (2) higher incidence in older population; (3) occurrence in conjunction with identifiable underlying autoimmune diseases, lymphoproliferative or solid tumor malignancies, pregnancy, and use of certain antibiotics such as penicillin and sulfonamides in approximately 50% of cases; and (4) in vitro inhibitor activity that follow a type II pharmacokinetic pattern with incomplete neutralization of the targeted clotting factor activity by the autoantibody, typically resulting in residual factor VIII levels ranging between 2%-18% in patient plasma.

The peptide or composition of the present invention may be administered to a patient with acquired haemophilia, or to a patient believed to be at risk of developing acquired haemophilia due to, for example:
 i) imminent treatment with, for example penicillin or a sulformamide
 ii) progression of a tumour or other malignancy
 iii) imminent or early pregnancy.

The invention will now be further described by way of Examples, which are meant to serve to assist one of ordinary skill in the art in carrying out the invention and are not intended in any way to limit the scope of the invention.

EXAMPLES

Example 1

Selection of HLA-DR2 Factor VIII Peptides

A series of FDVIII 15mer peptides were compared using three HLA-DR binding algorithms:
SYFPEITHI (http colon-slash-slash www.syfpeithi.de/home)
ProPred (http colon-slash-slash www.imtech.res.in/raghava/propred/) and
IEDB (http colon-slash-slash www.immuneepitope.org/home.do).
Peptides were selected which were predicted to be HLA-DR2-binding by more than one of the programmes and flanking sequences were designed for the predicted core residues (table 2).

TABLE 2

| Peptide No | FVIII First AA | Sequence in single amino acid code | Also referred to herein as: |
|---|---|---|---|
| 1 | 2140 | GTLMVFFGNVDSSGI | GTLMV |
| 2 | 0208 | TQTLHKFILLFAVFD | TQTLH |
| 3 | 2114 | SLYISQFIIMYSLDG | SLYIS |
| 4 | 2161 | PPIIARYIRLHPTHY | PPIIA |
| 5 | 2318 | PPLLTRYLRIHPQSW | PPLLT |
| 6 | 250 | MHTVNGYVNRSLPGL | MHTVN |
| 7 | 322 | LGQFLLFCHISSHQH | LGQFL |
| 8 | 478 | DTLLIIFKNQASRPY | DTLLI |
| 9 | 545 | PRCLTRYYSSFVNME | PRCLT |
| 10 | 607 | TENIQRFLPNPAGVQ | TENIQ |
| 11 | 1788 | DNIMVTFRNQASRPY | DNIMV |
| 12 | 2322 | RYLRIHPQSWVHQIA | RYLRI |

Example 2

Investigating the Response of HLA-DR2 Restricted Cells from Factor VIII Immunised Mice to Peptides HLA-DR2 transgenic mice were immunised with human factor VIII in adjuvant. Draining lymph node cells were collected and restimulated in vitro with different concentrations of the 12 peptides from table 2. The results are shown in FIG. 1.

HLA-DR2 restricted cells from factor VIII immunised mice clearly respond strongly to peptide DNIMV (SEQ ID NO: 11) ($1^{st}$ amino acid 1788). There are also responses to peptides PRCLT (SEQ ID NO: 9) (545) and PPIIA (SEQ ID NO: 4) (2161).

Example 3

Investigating the Response of T Cells from HLA-DR2 Mice to Peptides

HLA-DR2 mice were first immunised with factor VIII in adjuvant. Spleen cells from immune mice were restimulated in vitro with factor VIII and the resulting lymphoblasts were fused with the BW5147 thymoma using polyethylene glycol.

Figure 2:
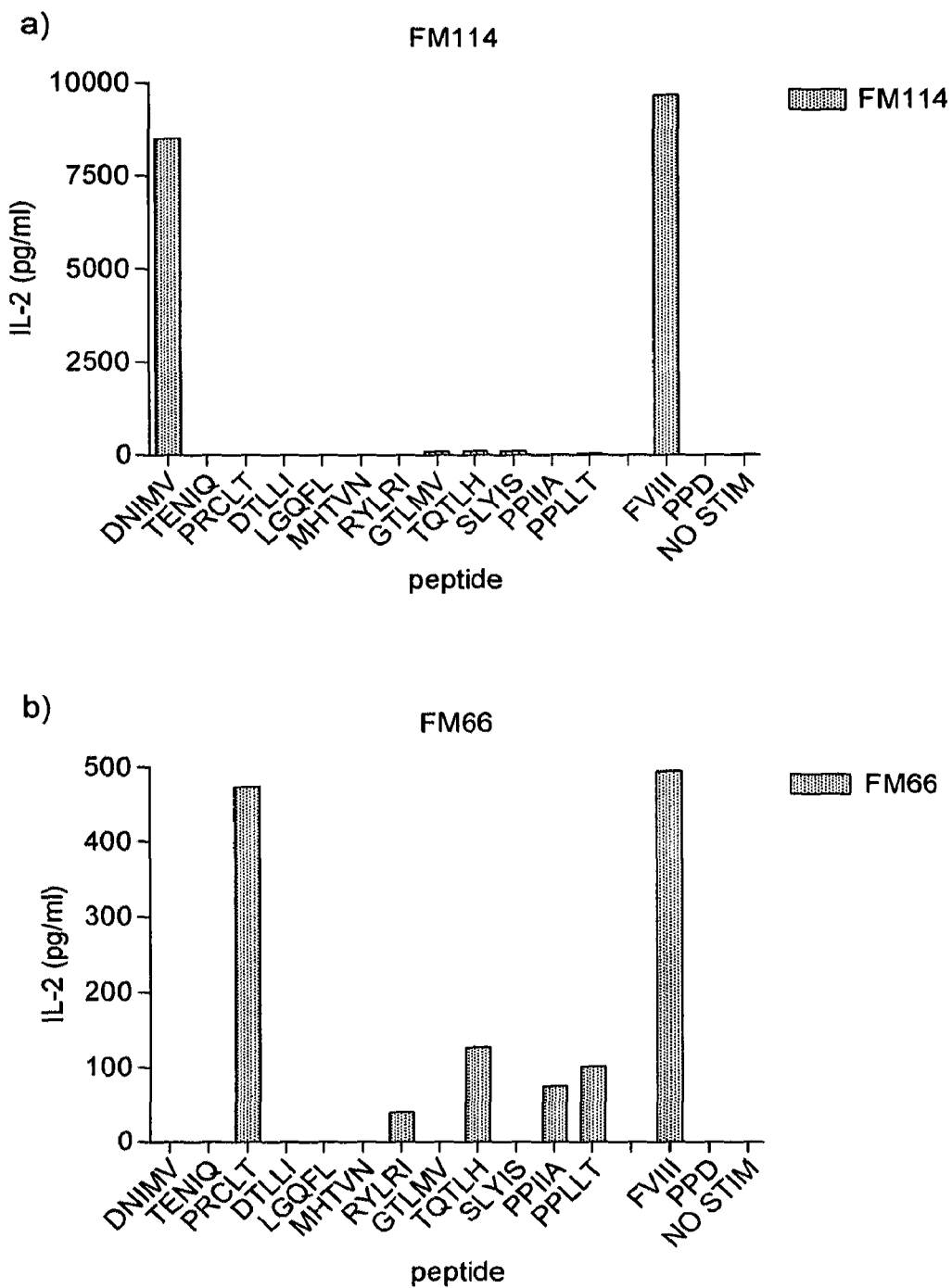
FIG. 2: Representative examples of FVIII+DR2+ T cell hybridoma clones specific for FVIII-derived peptides

T-cell hybridomas were selected in HAT medium and the hybridomas cloned and tested for their response to factor VIII. The hybridomas were then screened for their response to the 12 predicted peptides. Of the 27 hybridomas screened, 11 responded to DNIMV (SEQ ID NO: 11), 3 to PRCLT (SEQ ID NO: 9) and 3 to PPIIA (SEQ ID NO: 4), although the response to PPIIA (SEQ ID NO: 4) was weaker and less specific. The response of two hybridomas specific for DNIMV (SEQ ID NO: 11) and PRCLT (SEQ ID NO: 9) is shown in FIG. 2.

Example 4

Investigating the Response of Lymph Node Cells from FVIII–DR2+ Mice to Peptides

HLA-DR2 transgenic mice were crossed with factor VIII deficient mice to create a model of haemophilia expressing the human HLA class II MHC molecule.

Figure 3:
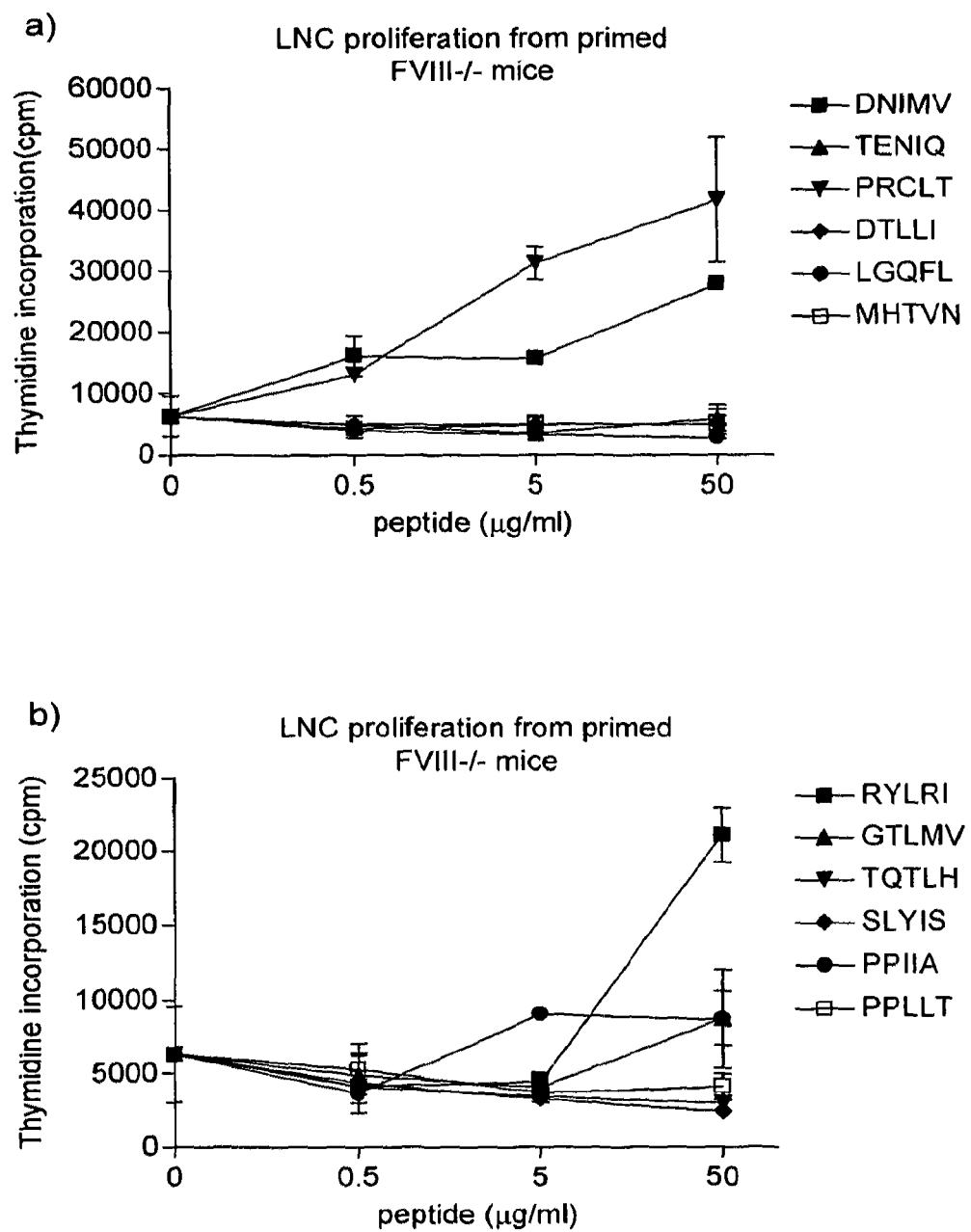
FIG. 3: Recall responses for LNC from FVIII−DR2+ mice primed with rhFVIII/CFA
Figure 3:
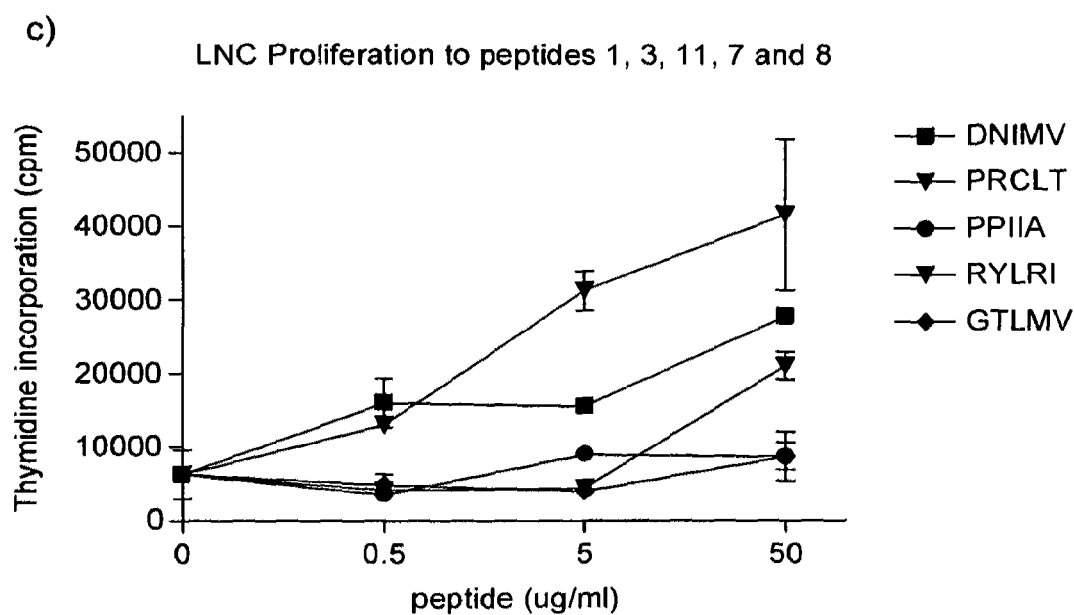

These FVIII-DR2+ animals were immunised with factor VIII in adjuvant. Draining lymph nodes were isolated and tested for their response to the peptide panel. As shown in FIG. 3. these cells responded well to PRCLT (SEQ ID NO: 9) and DNIMV (SEQ ID NO: 11). There was a weak response to GTLMV (SEQ ID NO: 13) and significant response to RYLRI (SEQ ID NO: 12).

Example 5

Investigating the Response of T Cells from HLA-DR2 Mice to Peptides

Figure 4:
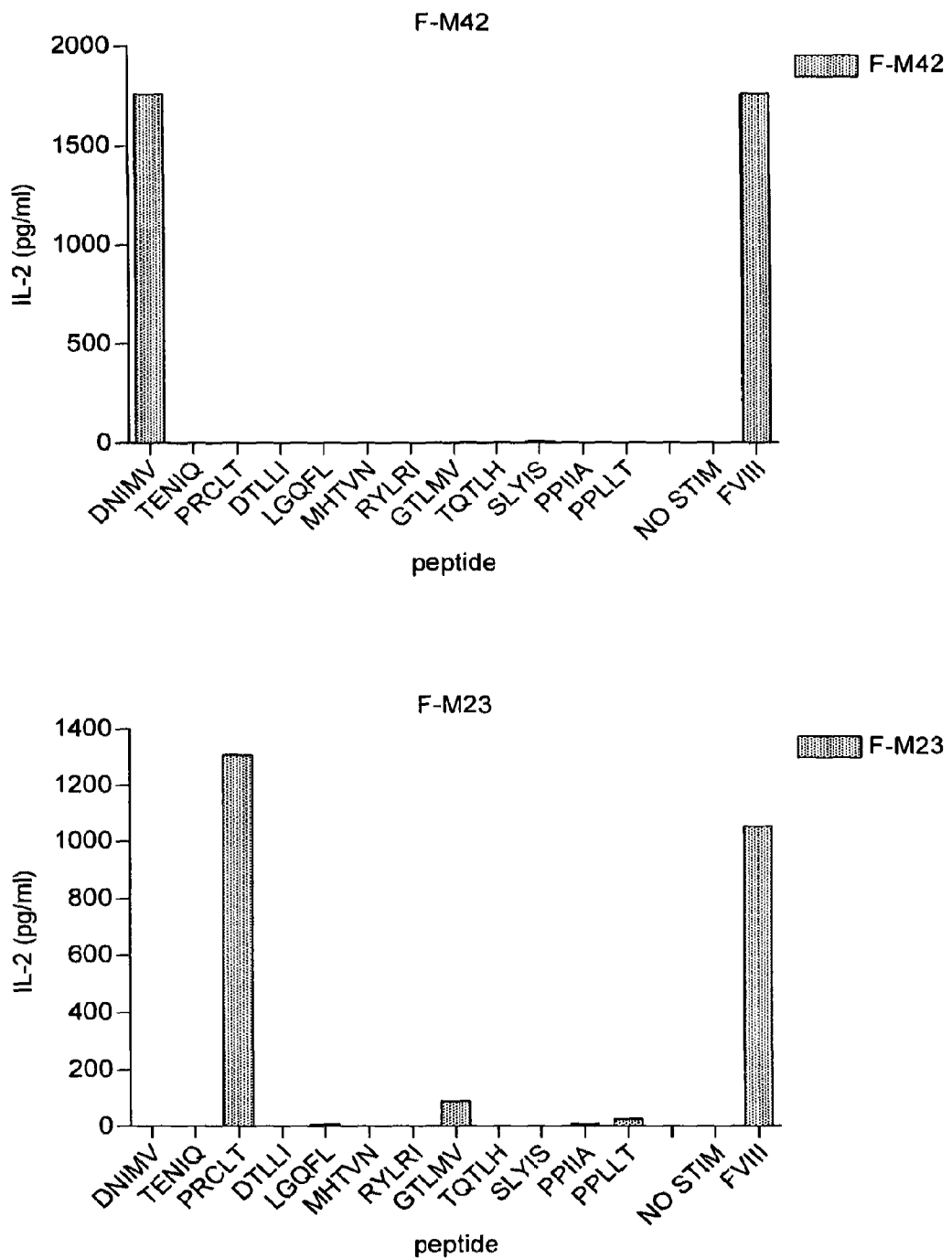
FIG. 4: Representative examples of FVIII−DR2+ T cell hybridoma clones specific for FVIII-derived peptides
Figure 4:
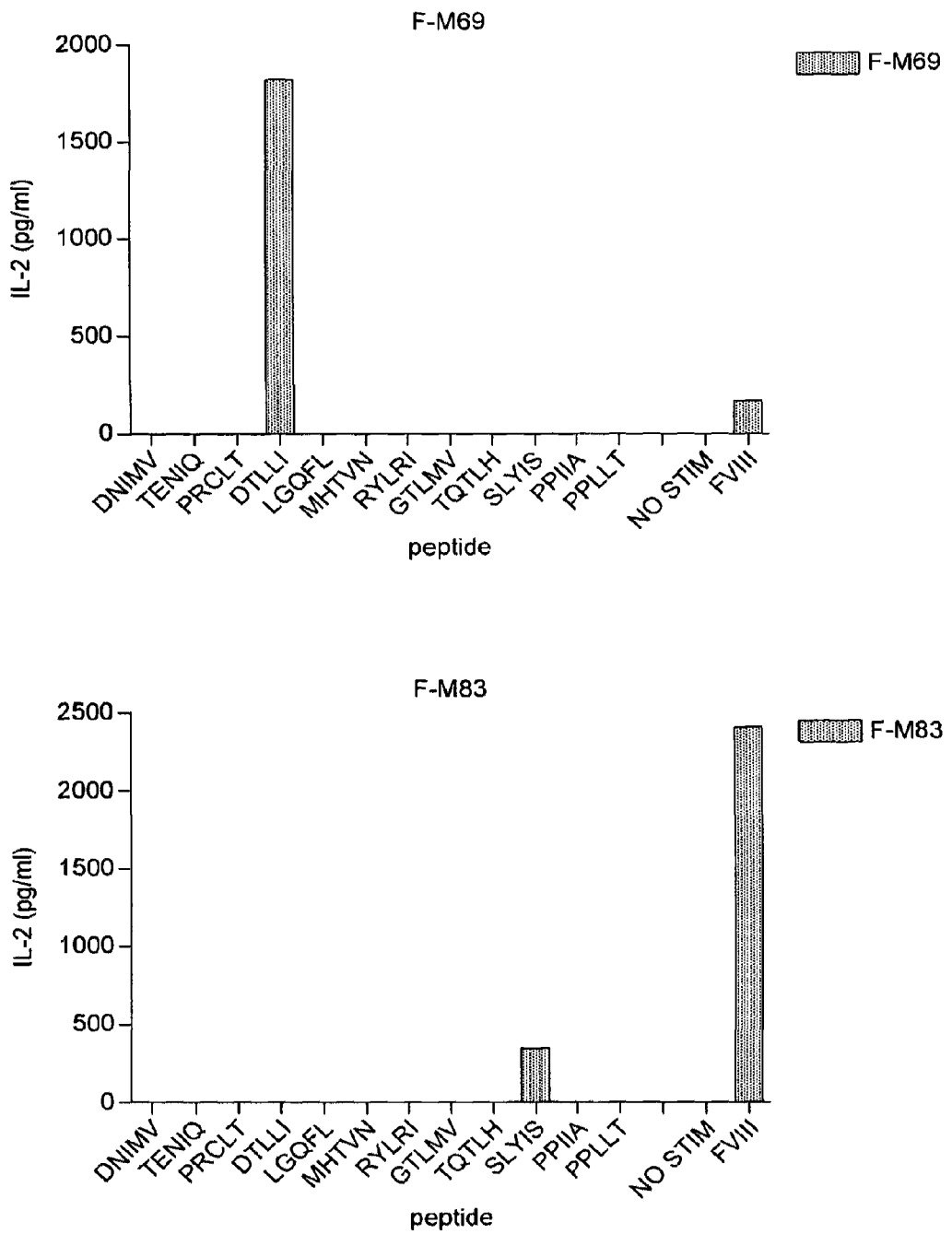

Factor VIII deficient mice expressing HLA-DR2 were immunised with factor VIII in adjuvant. Spleen cells from the immunised mice were restimulated in vitro with factor VIII and the resulting lymphoblasts were fused with BW5147, as described above. T-cell hybridomas were screened for their response to the 12 predicted peptides. Yet again, the majority of hybridomas responded to peptides DNIMV (SEQ ID NO: 11) and PRCLT (SEQ ID NO: 9). Of 19 hybridomas specific for factor VIII, 10 responded to DNIMV (SEQ ID NO: 11), 6 to PRCLT (SEQ ID NO: 9), 1 to PPIIA (SEQ ID NO: 4), 1 to SLYIS (SEQ ID NO: 3) and 1 to DTLLI (SEQ ID NO: 8). Examples of responses by these hybridomas are shown in FIG. 4.

Based on these experiments it is clear that two peptides DNIMV (SEQ ID NO: 11) (first amino acid number 1788) and PRCLT (SEQ ID NO: 9) (first amino acid 545) constitute the immunodominant T-cell epitopes in the HLA-DR2 restricted T-cell response to human factor VIII.

Example 6

DNIMV and PRCLT Behave as Apitopes

In order to be an apitope, a peptide must be capable of binding to an MHC class I or II molecule without further antigen processing (i.e. trimming) and be presented to a T cell. In the present case, the capacity of peptides to be presented by fixed APC was investigated.

Figure 5:
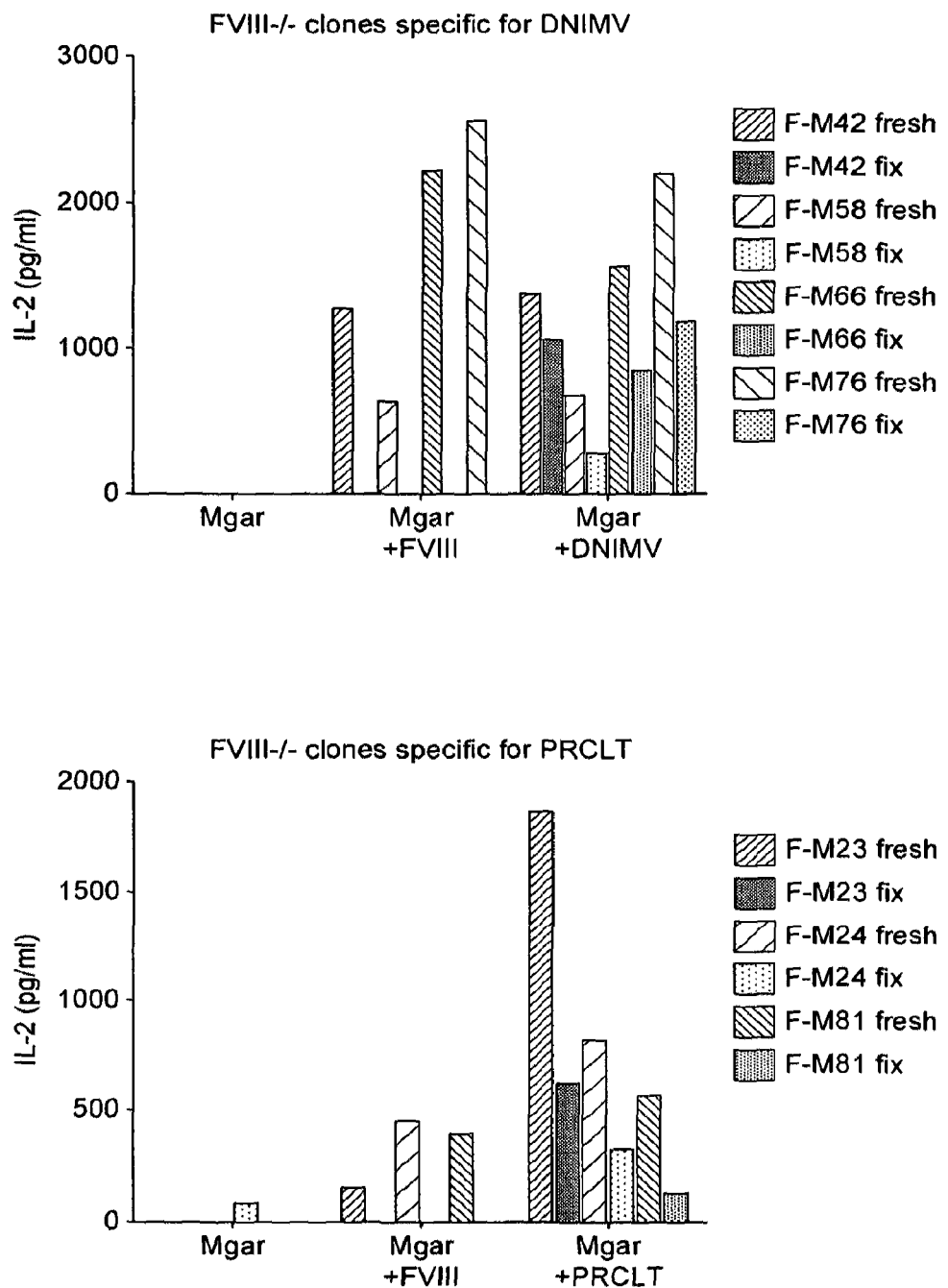
FIG. 5: FVIII−/− clones specific for a) DNIMV and b) PRCLT

Mgar cells were either fresh or fixed with 1% paraformaldehyde. Clones were tested for antigenic specificity by culturing 100 μl of hybridoma cells with 5×10$^4$ Mgar cells in the presence and absence of 20 μg/ml rhFVIII or peptide epitopes overnight. Supernatants were then collected and assessed for IL-2 production by ELISA. The fact that rhFVIII must be presented by live Mgar cells demonstrates that the intact protein requires antigen processing to be presented. Peptides DNIMV (SEQ ID NO: 11) and PRCLT (SEQ ID NO: 9), on the other hand, are presented by both live and fixed mgar cells indicating that these peptides function as apitopes (FIG. 5).

Example 7

Figure 7A:
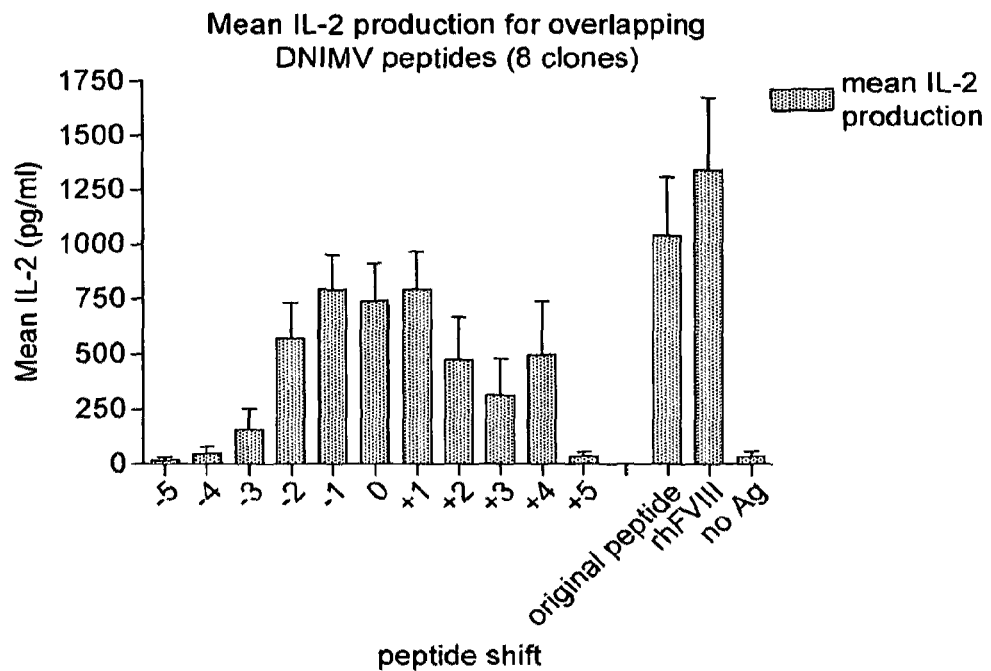
FIG. 7: Determination of the range of peptide epitopes capable of functions as apitopes using FVIII−DR2+ T cell hybridoma clones specific for FVIII-derived overlapping peptides. The original peptide is termed 0. One amino acid shift towards the N-terminal is −1, two amino acid shifts towards the N-terminal is −2 etc. One shift towards the C-terminal is +1 etc.
Figure 7B:
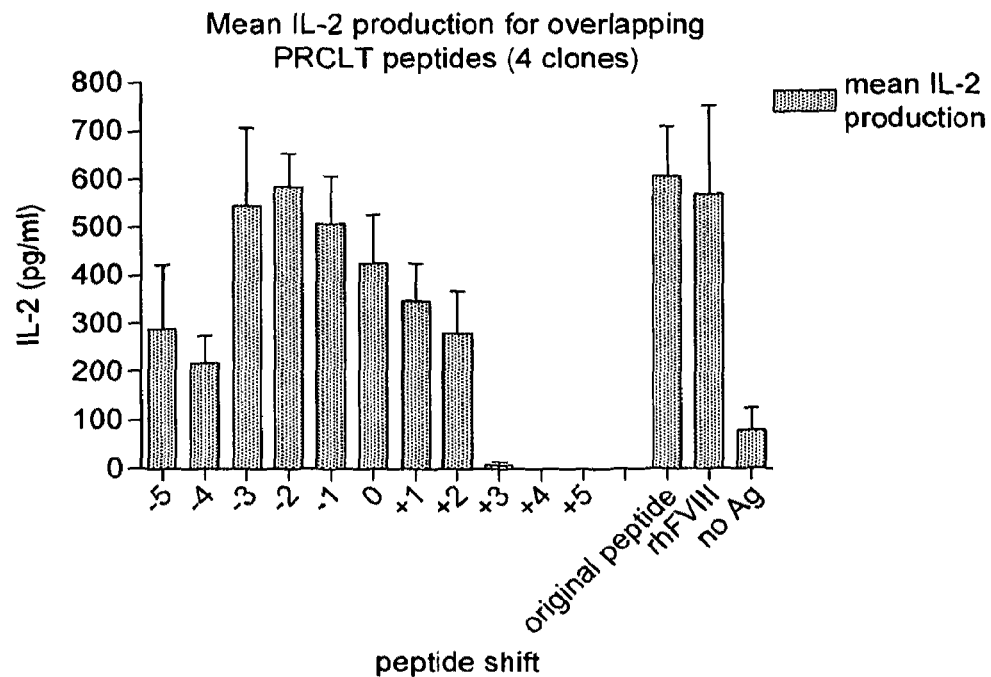
Figure 7C:
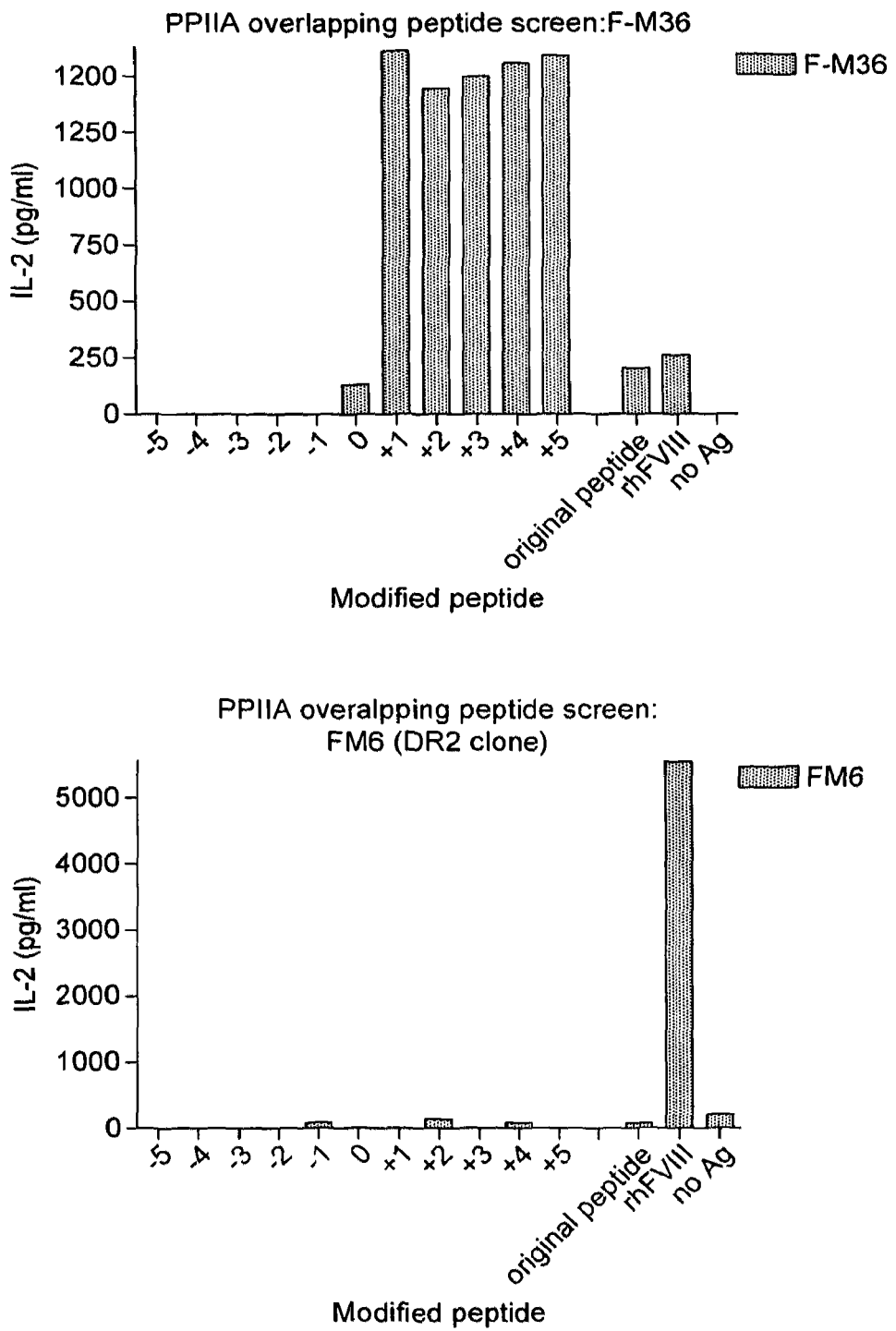
Figure 7:
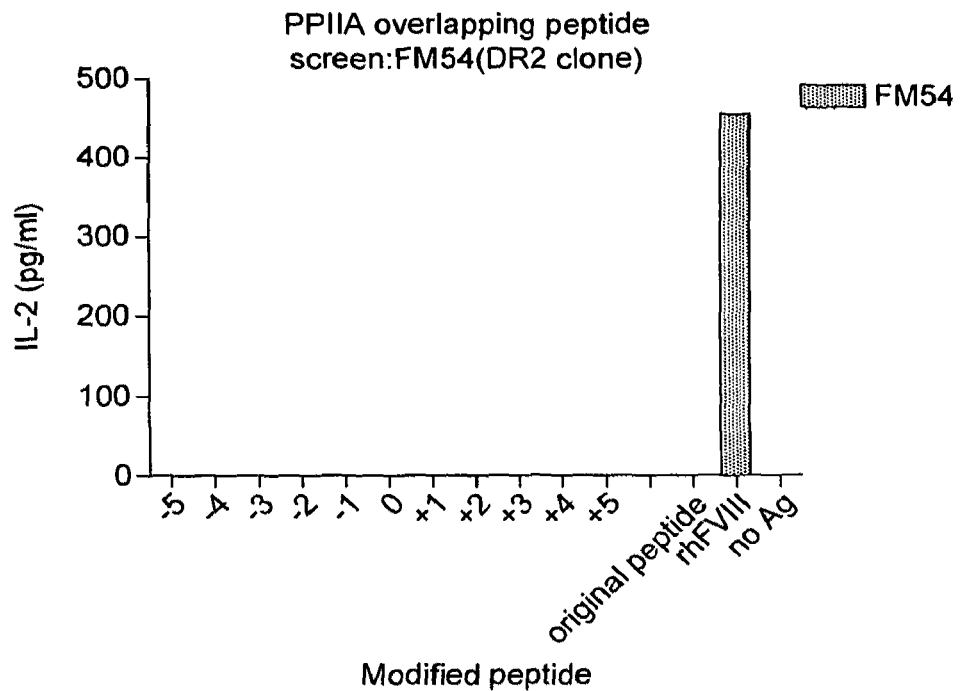
Figure 7:
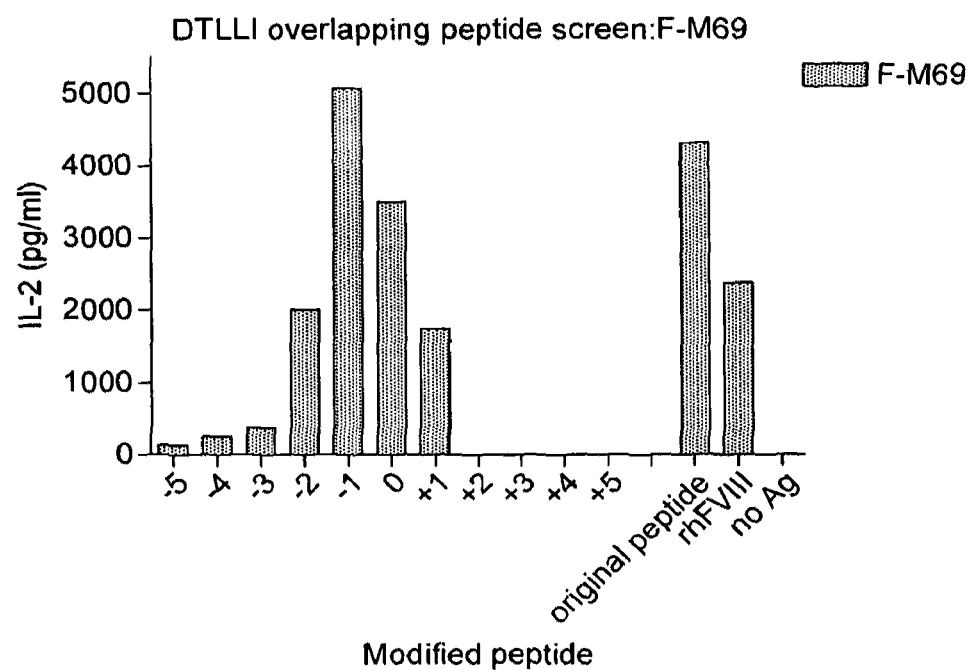
Figure 7:
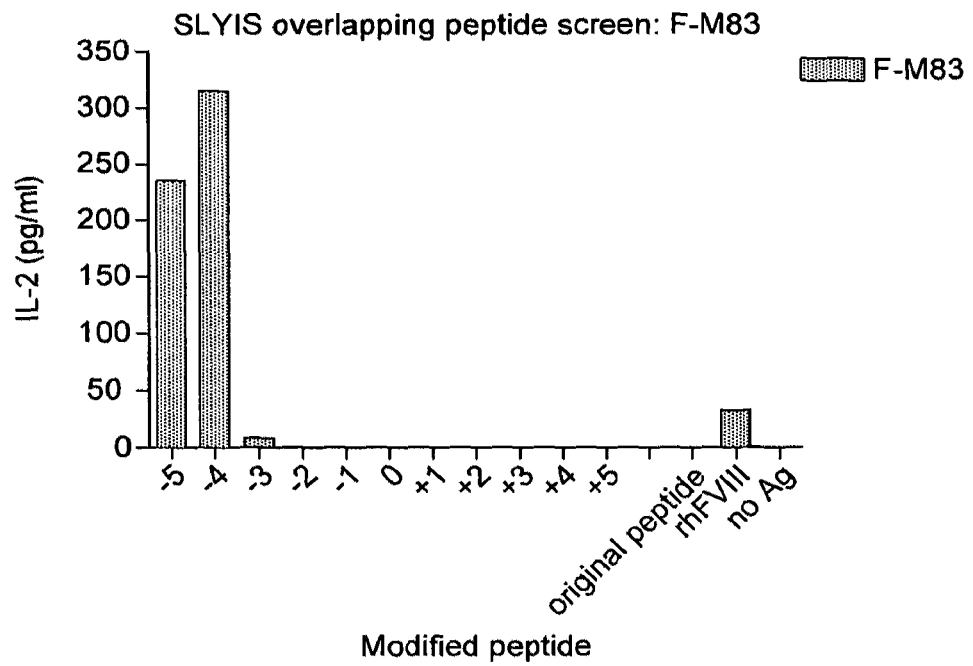
Figure 7:
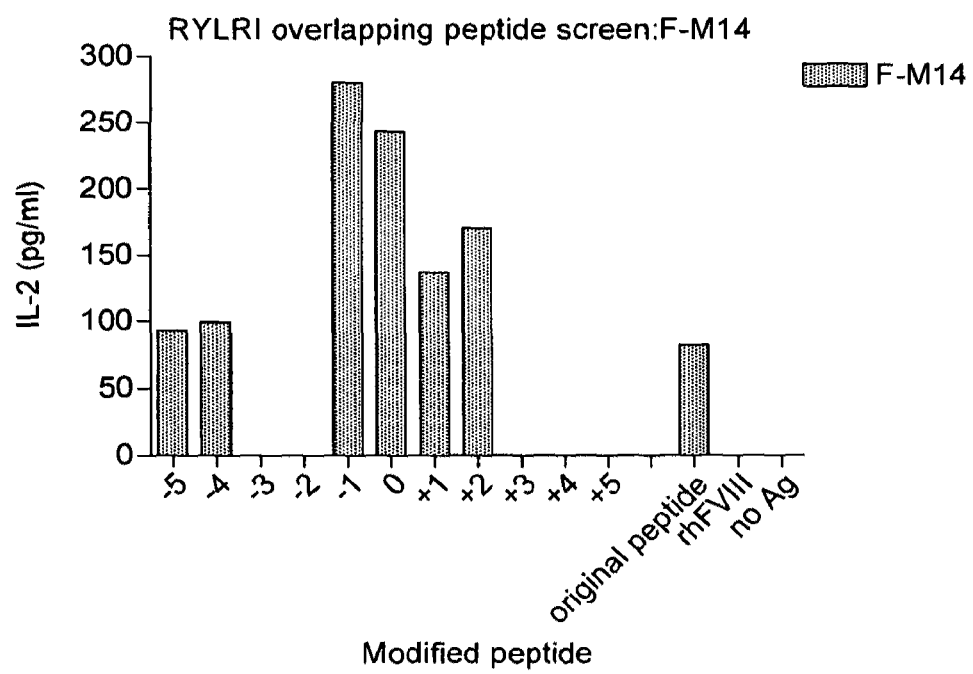

Determination of the Range of Peptide Epitopes Capable of Functioning as Apitopes The range of peptide epitopes capable of functioning as apitopes in the sequences surrounding DNIMV (SEQ ID NO: 11), PRCLT (SEQ ID NO: 9) and the other peptides was identified by preparing panels of overlapping peptides (shown on pages 36-37) and screening these using the T-cell hybridomas using the same method as Example 5 (FIG. 7).

Example 8

DNIMV and PRCLT Induce Tolerance to Whole Factor VIII Protein

Figure 6:
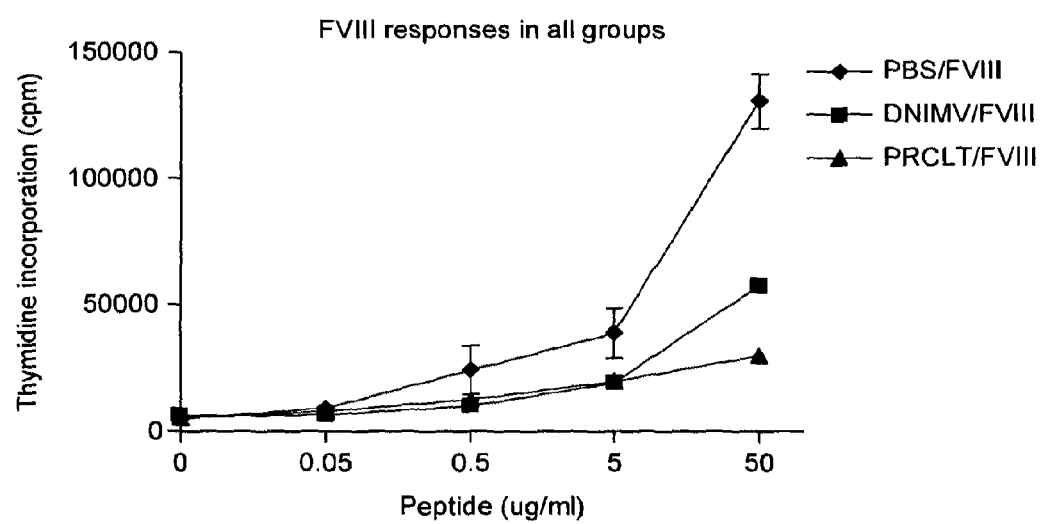
FIG. 6: Recall responses for LNC to FVIII for FVIII+ DR2+ mice treated 3× i.p. with peptide prior to priming with rhFVIII/CFA

HLA-DR2 transgenic mice were treated with either of the two soluble peptides, or PBS as a control, prior to immunisation with factor VIII in adjuvant. Draining lymph nodes were isolated and the cells restimulated in vitro with factor VIII protein in order to assess the immune status of the mice. As shown in FIG. 6, treatment of mice with either DNIMV (SEQ ID NO: 11) or PRCLT (SEQ ID NO: 9) led to a substantial suppression of the immune response to factor VIII.

Example 9

Investigation of Whether DNIMV and PRCLT Able to Induce Tolerance in the Factor VIII Knockout Mouse It was known from Example 8 that these two peptides are able to prevent the immune response to factor VIII in mice expressing endogenous factor VIII. The experiment was repeated with FVIII–DR2+ animals to determine whether these peptides also prevent the immune response to factor VIII in factor VIII deficient mice.

Example 10

Figure 8:
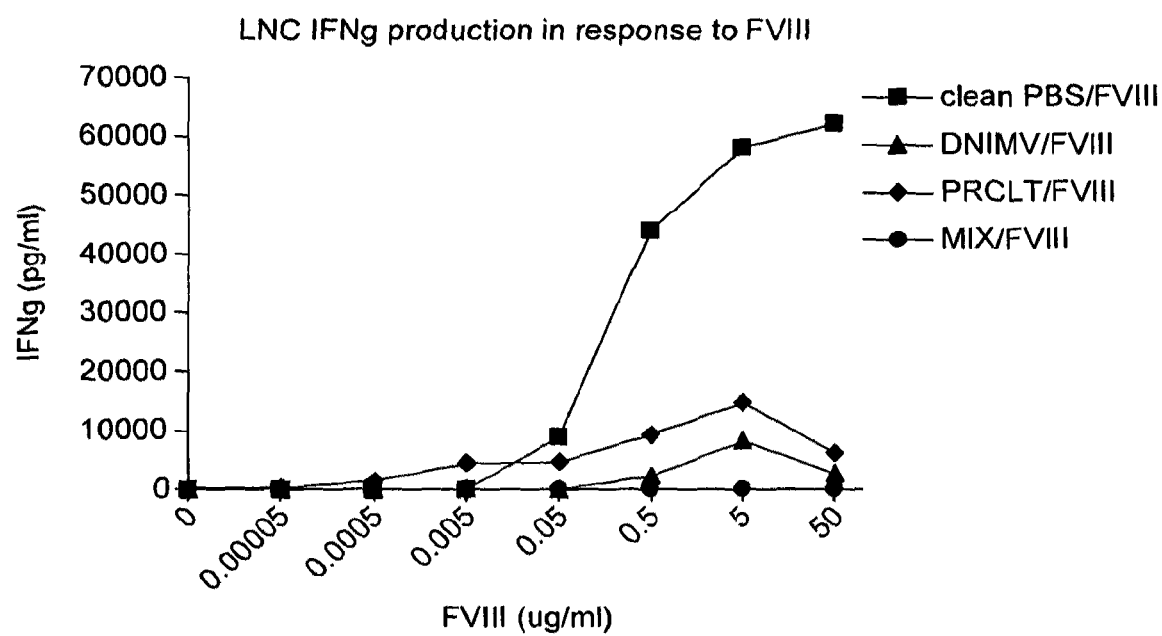
FIG. 8: Lymph node cell IFN-gamma production in response to FVIII for FVIII−DR2+ mice treated with FVIII-derived peptides PRCLT, DNIMV or a mixture of both of these.

Investigation of Whether DNIMV and PRCLT in Combination are Able to Induce Tolerance in the Factor VIII Knockout Mouse The two peptides which were shown to individually reduce the immune response to factor VIII in factor VIII deficient mice in Example 9 were combined. As shown in FIG. 8, treatment of mice with both DNIMV (SEQ ID NO: 11) and PRCLT (SEQ ID NO: 9) led to a substantial suppression of the immune response to factor VIII, as shown by the decrease in IFN-gamma production. IFN-gamma is the major class switch lymphokine required for neutralising antibodies in the mouse. The effect demonstrated was greater than that observed using either peptide alone.

Example 11

The Induction of Tolerance Using a Modified Peptide

The peptide DNIMV (SEQ ID NO: 11) is partly, but not completely soluble. In order to improve the solubility of the peptide, a modified version was designed with the following sequence: EDNIMVTFRNQASR (SEQ ID NO: 23).

This is extended at the N-terminus to add a charged hydrophilic residue. It is also a truncated at the C-terminus to remove the proline and tyrosine residues. Furthermore by placing positively and negatively charged amino acids at either end of the peptide a charge dipole is created reported to increase solubility.

Figure 9:
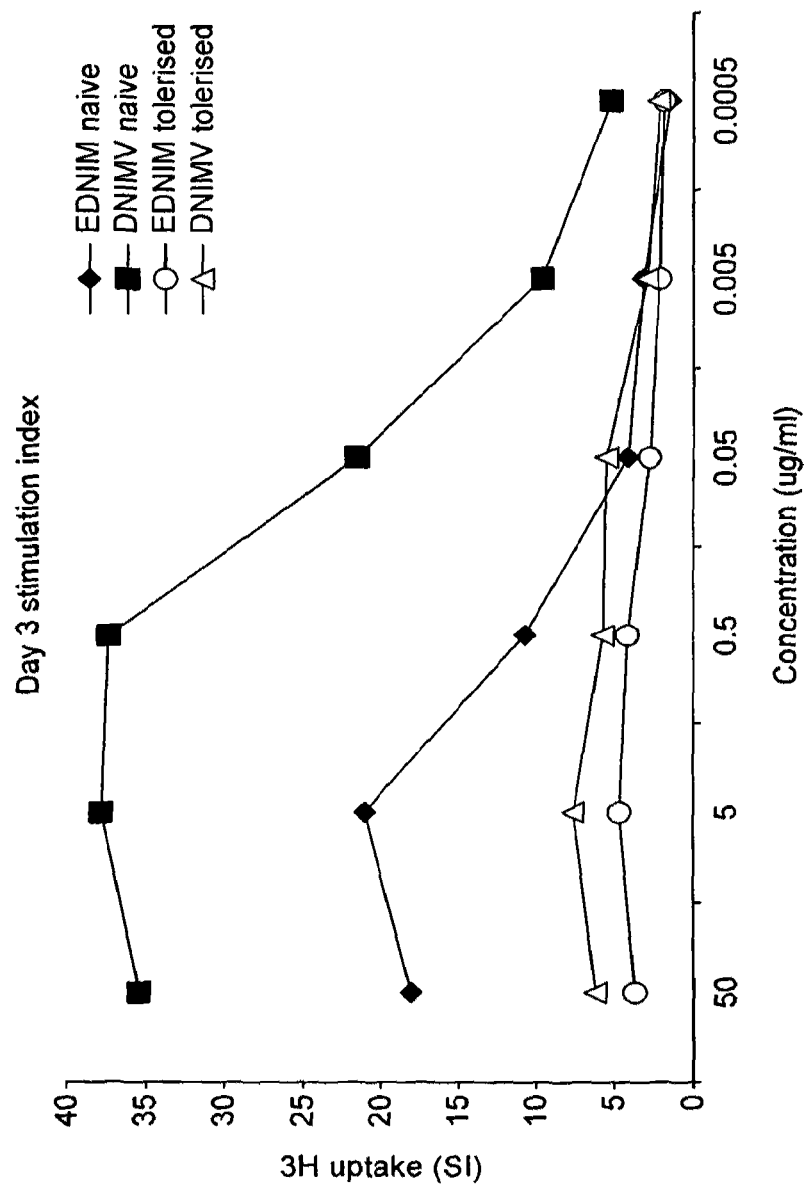
FIG. 9: Responses from naive or tolerised mice stimulated with either EDNIMVTFRNQASR (EDNIMV) or a control peptide (DNIMV).

The modified peptide is more soluble than DNIMV (SEQ ID NO: 11) and sufficiently soluble to allow intranasal peptide delivery. In order to assess the induction of tolerance using this peptide epitope, FVIII deficient mice were taken and half treated with the modified EDNIMV (SEQ ID NO: 23) peptide (referred to as 'tolerised' in FIG. 9). The mice were then immunised with DNIMV (SEQ ID NO: 11) in CFA and 10 days later draining lymph nodes were collected and stimulated in vitro with either DNIMV (SEQ ID NO: 11) or EDNIMV (SEQ ID NO: 23). FIG. 9 shows the results for responses from either naïve or tolerised mice stimulated with either DNIMV (SEQ ID NO: 11) or EDNIMV (SEQ ID NO: 23) in vitro.

The results demonstrate that EDNIMV (SEQ ID NO: 23) is able to recall an immune response from mice immunised with DNIMV (SEQ ID NO: 11). Furthermore, they demonstrate very clearly that mice tolerized with EDNIMV (SEQ ID NO: 23) fail to mount an immune response to DNIMV (SEQ ID NO: 11) in vivo as revealed by the lack of response to either DNIMV (SEQ ID NO: 11) or EDNIMV (SEQ ID NO: 23) in vitro after priming with DNIMV (SEQ ID NO: 11) in CFA.

Example 12

EDNIMV (SEQ ID NO: 23) Induces Tolerance to Whole Factor VIII Protein

The experiment described in Example 8 is repeated for the modified peptide EDNIMV (SEQ ID NO: 23) to demonstrate that EDNIMV (SEQ ID NO: 23) is able to suppress the immune response to the whole factor VIII protein.

Methods (i) Recall Responses for DR2+ Mice Primed with rhFVIII

HLA-DR2+ murine MHC class II null mice were immunised with 40 μg rhFVIII emulsified in Complete Freunds Adjuvant supplemented with 400 μg heat-killed *M. tuberculosis* H37Ra, subcutaneously at the base of the tail. 10 days later the mice were sacrificed and the draining lymph nodes removed. Single cell suspensions were prepared and lymphocytes incubated at 4-$5\times10^5$ cells per well in 96-well flat bottomed plates for 72 hours with the indicated concentrations of peptide or control antigens before pulsing with 0.5 μCi/well tritiated thymidine for a further 16 hours. Plates were then frozen before cells were harvested onto glass filter mats and radioactive incorporation measured using a liquid scintillation β-counter (ii) FVIII Peptide Specificity of T Cell Hybridomas Generated from DR2+ Mice HLA-DR2+ murine MHC class II null mice were immunised as above. On day 10 draining lymph nodes were removed and lymphocytes cultured at $2.5\times10^6$ cells/ml, 1 ml/well in 24 well plates in the presence of 20 μg/ml rhFVIII for 3 days. Following this stimulation, lymphocytes were recovered, washed and fused with $TCR\alpha^-\beta^-$ BW fusion partner cells at a ratio of 4 BW cells to 1 lymphocyte, using polyethylene glycol as described by Nelson et al (1980) *PNAS* 77(5):2866. Fused cells were carefully washed and then plated out in flat bottomed 96 well plates for 2 days before the addition of HAT medium to select for T cell hybridomas. Cells were monitored for growth and approximately 10 days after fusions were performed, individual clones were selected and transferred to 24 well plates in HAT medium. Clones were maintained in HAT medium for at least 2 weeks before being weaned into HT medium and then complete medium. Clones were tested for antigenic specificity by culturing 100 μl of hybridoma cells with $5\times10^4$ Mgar cells in the presence and absence of 20 μg/ml rhFVIII overnight. Supernatants were then collected and assessed for IL-2 production by ELISA, with clones producing IL-2 in response to rhFVIII being considered positive for FVIII-specificity. To investigate the repertoire of predicted FVIII peptides FVIII-specific clones were again tested for IL-2 production, following overnight incubation with 20 μg/ml of each of the 12 peptides.

(iii) Recall Responses for FVIII−/− Mice Primed with rhFVIII

The same method was followed as for (i), except the mice were FVIII-deficient, HLA-DR2+ and murine MHC class II null.

(iv) FVIII Peptide Specificity of T Cell Hybridomas Generated from FVIII−/− Mice The same method was followed as for (ii), except the mice were FVIII-deficient and HLA-DR2+.

(V) Tolerisation of FVIII-Specific Responses in DR2+Mice by Pre-Treatment with Immunodominant FVIII Peptides HLA-DR2+ murine MHC class II null mice were treated 3 times with 100 μg of DNIMV (SEQ ID NO: 11), PRCLT (SEQ ID NO: 9) or PPIIA (SEQ ID NO: 4) dissolved in PBS, or the equivalent volume of PBS alone. Peptides were administered intraperitoneally, with 3-4 days between each dose. Following the final administration, mice were primed with rhFVIII emulsified in complete Freunds adjuvant as for (i). 10 days later, draining lymph nodes were recovered and lymphocytes subsequently cultured in vitro with rhFVIII, or each of the tolerising peptides as well as control antigens, for 72 hours before the addition of tritiated thymidine as for (i). (vi) Tolerisation of FVIII-Specific Responses in DR2+Mice by Pre-Treatment with a Combination Immunodominant FVIII Peptides HLA-DR2+ murine MHC class II null mice were treated 3 times with DNIMV (SEQ ID NO: 11), PRCLT (SEQ ID NO: 9) or a combination of both DNIMV (SEQ ID NO: 11) and PRCLT (SEQ ID NO: 9) dissolved in PBS, or the equivalent volume of PBS alone. Peptides were administered intraperitoneally, over 8 days. Following the final administration, mice were primed with rhFVIII emulsified in complete Freunds adjuvant as for (i). 10 days later, draining lymph nodes were recovered and lymphocytes subsequently re-stimulated in vitro with rhFVIII. The supernatants were then collected and IFN-gamma was measured.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular immunology or related fields are intended to be within the scope of the following claims.

SEQ ID No. 1

```
  1 mqielstcff lcllrfcfsa trryylgave lswdymqsdl gelpvdarfp prvpksfpfn 61 tsvvykktlf veftdhlfni akprppwmgl lgptiqaevy dtvvitlknm ashpvslhav 121 gvsywkaseg aeyddqtsqr ekeddkvfpg gshtyvwqvl kengpmasdp lcltysylsh 181 vdlvkdlnsg ligallvcre gslakektqt lhkfillfav fdegkswhse tknslmqdrd 241 aasarawpkm htvngyvnrs lpgligchrk svywhvigmg ttpevhsifl eghtflvrnh 301 rqasleispi tfltaqtllm dlgqfllfch isshqhdgme ayvkvdscpe epqlrmknne 361 eaedydddlt dsemdvvrfd ddnspsfiqi rsvakkhpkt wvhyiaaeee dwdyaplvla 421 pddrsyksqy lnngpqrigr kykkvrfmay tdetfktrea iqhesgilgp llygevgdtl 481 liifknqasr pyniyphgit dvrplysrrl pkgvkhlkdf pilpgeifky kwtvtvedgp 541 tksdprcltr yyssfvnmer dlasgligpl licykesvdq rgnqimsdkr nvilfsvfde 601 nrswylteni qrflpnpagv qledpefqas nimhsingyv fdslqlsvcl hevaywyils
```

-continued

```
 661 igaqtdflsv ffsgytfkhk mvyedtltlf pfsgetvfms menpglwilg chnsdfrnrg
 721 mtallkvssc dkntgdyyed syedisayll sknnaieprs fsqnsrhpst rqkqfnatti
 781 pendiektdp wfahrtpmpk iqnvsssdll mllrqsptph glslsdlqea kyetfsddps
 841 pgaidsnnsl semthfrpql hhsgdmvftp esglqlrine klgttaatel kkldfkvsst
 901 snnlistips dnlaagtdnt sslgppsmpv hydsqldttl fgkkssplte sggplslsee
 961 nndskllesg lmnsqesswg knvsstesgr lfkgkrahgp alltkdnalf kvsisllktn
1021 ktsnnsatnr kthidgpsll ienspsvwqn ilesdtefkk vtplihdrml mdknatalrl
1081 nhmsnkttss knmemvqqkk egpippdaqn pdmsffkmlf lpesarwiqr thgknslnsg
1141 qgpspkqlvs lgpeksvegq nflseknkvv vgkgeftkdv glkemvfpss rnlfltnldn
1201 lhennthnqe kkiqeeiekk etliqenvvl pqihtvtgtk nfmknlflls trqnvegsyd
1261 gayapvlqdf rslndstnrt kkhtahfskk geeenleglg nqtkqiveky acttrispnt
1321 sqqnfvtqrs kralkqfilp leetelekri ivddtstqws knmkhltpst ltqidyneke
1381 kgaitqspls dcltrshsip qanrsplpia kvssfpsirp iyltrvlfqd nsshlpaasy
1441 rkkdsgvqes shflqgakkn nislailtie mtgdqrevgs lgtsatnsvt ykkventvip
1501 kpdlpktsgk vellpkvhiy qkdlfptets ngspghldlv egsllqgteg aikwneanrp
1561 gkvpflrvat essaktpskl ldplawdnhy gtqipkeewk sqekspekta fkkkdtilsl
1621 nacesnhaia ainegqnkpe ievtwakqgr terlcsqnpp vlkrhqreit rttlqsdqee
1681 idyddtisve mkkedfdiyd edenqsprsf qkktrhyfia averlwdygm sssphvlrnr
1741 aqsgsvpqfk kvvfqeftdg sftqplyrge lnehlgllgp yiraevedni mvtfrnqasr
1801 pysfysslis yeedqrqgae prknfvkpne tktyfwkvqh hmaptkdefd ckawayfsdv
1861 dlekdvhsgl igpllvchtn tlnpahgrqv tvqefalfft ifdetkswyf tenmerncra
1921 pcniqmedpt fkenyrfhai ngyimdtlpg lvmaqdqrir wyllsmgsne nihsihfsgh
1981 vftvrkkeey kmalynlypg vfetvemlps kagiwrvecl igehlhagms tlflvysnkc
2041 qtplgmasgh irdfqitasg qygqwapkla rlhysgsina wstkepfswi kvdllapmii
2101 hgiktqgarq kfsslyisqf iimysldgkk wqtyrgnstg tlmvffgnvd ssgikhnifn
2161 ppiiaryirl hpthysirst lrmewmgcdl nscsmplgme skaisdaqit assyftnmfa
2221 twspskarlh lqgrsnawrp qvnnpkewlq vdfqktmkvt gyttqgvksl ltsmyvkefl
2281 isssqdghqw tlffqngkvk vfqgnqdsft pvvnsldppl ltrylrihpq swvhqialrm
2341 evlgceaqdl y
```

Overlapping Peptide Panels Prepared in Example 7

```
Overlapping set for DTLLIIFKNQASRPY
  1.  473-488         YGEVGDTLLIIFKNQ
  2.  474-489         GEVGDTLLIIFKNQA
  3.  475-490         EVGDTLLIIFKNQAS
  4.  476-491         VGDTLLIIFKNQASR
  5.  477-492         GDTLLIIFKNQASRP
  6.  478-493         DTLLIIFKNQASRPY
  7.  479-494         TLLIIFKNQASRPYN
  8.  480-495         LLIIFKNQASRPYNI
  9.  481-496         LIIFKNQASRPYNIY
 10.  482-497         IIFKNQASRPYNIYP
 11.  483-498         IFKNQASRPYNIYPH Overlapping set for PRCLTRYYSSFVNME
  1.  540-554         PTKSDPRCLTRYYSS
  2.  541-555         TKSDPRCLTRYYSSF
  3.  542-556         KSDPRCLTRYYSSFV
  4.  543-557         SDPRCLTRYYSSFVN
  5.  544-558         DPRCLTRYYSSFVNM
  6.  545-559         PRCLTRYYSSFVNME
  7.  546-560         RCLTRYYSSFVNMER
```

| | | -continued | | | -continued |
|---|---|---|---|---|---|
| 8. | 547-561 | CLTRYYSSFVNMERD | 10. | 2118-2132 | SQFIIMYSLDGKKWQ |
| 9. | 548-562 | LTRYYSSFVNMERDL | 11. | 2119-2133 | QFIIMYSLDGKKWQT |
| 10. | 549-563 | TRYYSSFVNMERDLA | | | |
| 11. | 550-564 | RYYSSFVNMERDLAS | | | |

Overlapping set for DNIMVTFRNQASRPY

Overlapping set for PPIIARYIRLHPTHY

| 1. | 1783-1797 | RAEVEDNIMVTFRNQ | 1. | 2156-2170 | HNIFNPPIIARYIRL |
|---|---|---|---|---|---|
| 2. | 1784-1798 | AEVEDNIMVTFRNQA | 2. | 2157-2171 | NIFNPPIIARYIRLH |
| 3. | 1785-1799 | EVEDNIMVTFRNQAS | 3. | 2158-2172 | IFNPPIIARYIRLHP |
| 4. | 1786-1800 | VEDNIMVTFRNQASR | 4. | 2159-2173 | FNPPIIARYIRLHPT |
| 5. | 1787-1801 | EDNIMVTFRNQASRP | 5. | 2160-2174 | NPPIIARYIRLHPTH |
| 6. | 1788-1802 | DNIMVTFRNQASRPY | 6. | 2161-2175 | PPIIARYIRLHPTHY |
| 7. | 1789-1803 | NIMVTFRNQASRPYS | 7. | 2162-2176 | PIIARYIRLHPTHYS |
| 8. | 1790-1804 | IMVTFRNQASRPYSF | 8. | 2163-2177 | IIARYIRLHPTHYSI |
| 9. | 1791-1805 | MVTFRNQASRPYSFY | 9. | 2164-2178 | IARYIRLHPTHYSIR |
| 10. | 1792-1806 | VTFRNQASRPYSFYS | 10. | 2165-2179 | ARYIRLHPTHYSIRS |
| 11. | 1793-1807 | TFRNQASRPYSFYSS | 11. | 2166-2180 | RYIRLHPTHYSIRST |

Overlapping set for SLYISQFIIMYSLDG

Overlapping set for RYLRIHPQSWVHQIA

| 1. | 2109-2123 | RQKFSSLYISQFIIM | 1. | 2317-2331 | PPLLTRYLRIHPQSW |
|---|---|---|---|---|---|
| 2. | 2110-2124 | QKFSSLYISQFIIMY | 2. | 2318-2332 | PLLTRYLRIBPQSWV |
| 3. | 2111-2125 | KFSSLYISQFIIMYS | 3. | 2319-2333 | LLTRYLRIHPQSWVH |
| 4. | 2112-2126 | FSSLYISQFIIMYSL | 4. | 2320-2334 | LTRYLRIHPQSWVHQ |
| 5. | 2113-2127 | SSLYISQFIIMYSLD | 5. | 2321-2335 | TRYLRIHPQSWVHQI |
| 6. | 2114-2128 | SLYISQFIIMYSLDG | 6. | 2322-2336 | RYLRIHPQSWVHQIA |
| 7. | 2115-2129 | LYISQFIIMYSLDGK | 7. | 2323-2337 | YLRIIPQSWVHQIAL |
| 8. | 2116-2130 | YISQFIIMYSLDGKK | 8. | 2324-2338 | LRIHPQSWVHQIALR |
| 9. | 2117-2131 | ISQFIIMYSLDGKKW | 9. | 2325-2339 | RIHPQSWVHQIALRM |
| | | | 10. | 2326-2340 | IHPQSWVHQIALRME |
| | | | 11. | 2327-2341 | HPQSWVHQIALRMEV |

---

The invention claimed is:

1. A peptide, the amino acid sequence of which consists of the amino acid sequence EDNIMVTFRNQASR (SEQ ID NO: 23), wherein the peptide binds to an MHC class II molecule without further antigen processing and is recognized by a factor VIII specific T cell.

2. A method for suppressing or preventing the production of factor VIII inhibitor antibodies in a subject with haemophilia A, which comprises the step of administering a peptide according to claim 1 to the subject.

3. A method according to claim 2, wherein the subject is undergoing, or is about to undergo, factor VIII replacement therapy.

4. A method according to claim 2, wherein the subject is HLA-DR2.

5. A method according to claim 3, wherein the subject is HLA-DR2.

6. A pharmaceutical composition comprising the peptide of claim 1 and a pharmaceutically acceptable excipient.

7. The method according to claim 2 that comprises administering to the subject a composition comprising the peptide and a pharmaceutically acceptable excipient.

8. A method according to claim 7, wherein the subject is undergoing, or is about to undergo, factor VIII replacement therapy.

9. A method according to claim 7, wherein the subject is HLA-DR2.

10. A method according to claim 8, wherein the subject is HLA-DR2.

* * * * *